US010052431B2

(12) United States Patent
Dreschel et al.

(10) Patent No.: US 10,052,431 B2
(45) Date of Patent: Aug. 21, 2018

(54) SYSTEM FOR MANIPULATION AND SORTING OF PARTICLES

(71) Applicant: Ascent Bio-Nano Technologies, Inc., State College, PA (US)

(72) Inventors: William Robert Dreschel, State College, PA (US); Yuchao Chen, State College, PA (US); Lin Wang, State College, PA (US)

(73) Assignee: Ascent Bio-Nano Technologies, Inc., State College, PA (US)

( * ) Notice: Subject to any disclaimer, the term of this patent is extended or adjusted under 35 U.S.C. 154(b) by 0 days.

(21) Appl. No.: 15/317,808

(22) PCT Filed: Jun. 9, 2015

(86) PCT No.: PCT/US2015/034836
§ 371 (c)(1),
(2) Date: Dec. 9, 2016

(87) PCT Pub. No.: WO2015/191534
PCT Pub. Date: Dec. 17, 2015

(65) Prior Publication Data
US 2017/0106134 A1    Apr. 20, 2017

Related U.S. Application Data

(60) Provisional application No. 62/009,550, filed on Jun. 9, 2014, provisional application No. 62/019,920, filed on Jul. 2, 2014.

(51) Int. Cl.
*B01D 3/00*    (2006.01)
*C02F 1/46*    (2006.01)
(Continued)

(52) U.S. Cl.
CPC ........ *A61M 1/3678* (2014.02); *A61M 1/3627* (2013.01); *B01D 21/283* (2013.01);
(Continued)

(58) Field of Classification Search
CPC .................. B01D 21/283; B01D 43/00; B01D 2021/0081; B01D 3/00; B01J 19/10; C02F 1/36; C02F 1/46
See application file for complete search history.

(56) References Cited

U.S. PATENT DOCUMENTS

| 4,055,491 A | 10/1977 | Porath-Furedi |
| 4,280,823 A | 7/1981 | Szonntagh |

(Continued)

FOREIGN PATENT DOCUMENTS

| EP | 2378267 A1 | 10/2011 |
| WO | 0004978 A1 | 2/2000 |

(Continued)

OTHER PUBLICATIONS

PCT, International Search Report and Written Opinion for International Patent Application No. PCT/US2015/034836 dated Mar. 5, 2016.

*Primary Examiner* — Walter D. Griffin
*Assistant Examiner* — Cameron J Allen
(74) *Attorney, Agent, or Firm* — Forrest Firm, P.C.

(57) ABSTRACT

A sound manipulation system is provided. The sound manipulation system includes a flow chamber arranged and disposed to receive a fluid containing a particulate and provide in-line sound wave manipulation of at least a portion of the particulate from the fluid, and a transducer positioned to facilitate the in-line sound wave manipulation within the flow chamber. The flow chamber includes at least a first portion and a second portion, the first portion being self-aligned and secured to the second portion.

38 Claims, 17 Drawing Sheets

(51) Int. Cl.
*A61M 1/36* (2006.01)
*B01L 3/00* (2006.01)
*B01D 21/28* (2006.01)

(52) U.S. Cl.
CPC ... *B01L 3/502707* (2013.01); *B01L 3/502761* (2013.01); *A61M 2205/3306* (2013.01); *A61M 2205/3317* (2013.01); *A61M 2205/3331* (2013.01); *A61M 2205/3337* (2013.01); *A61M 2205/52* (2013.01); *B01L 2300/0877* (2013.01); *B01L 2400/0436* (2013.01); *B01L 2400/0487* (2013.01)

(56) References Cited

U.S. PATENT DOCUMENTS

| | | | |
|---|---|---|---|
| 4,523,682 | A | 6/1985 | Barmatz et al. |
| 4,759,775 | A | 7/1988 | Peterson et al. |
| 4,983,189 | A | 1/1991 | Peterson et al. |
| 5,085,783 | A | 2/1992 | Feke et al. |
| 5,225,089 | A | 7/1993 | Benes et al. |
| 5,484,537 | A | 1/1996 | Whitworth |
| 5,527,460 | A | 6/1996 | Trampler et al. |
| 5,626,767 | A | 5/1997 | Trampler et al. |
| 5,688,405 | A | 11/1997 | Dickinson et al. |
| 5,711,888 | A | 1/1998 | Trampler et al. |
| 5,831,166 | A | 11/1998 | Kozuka et al. |
| 5,902,489 | A | 5/1999 | Yasuda et al. |
| 6,150,752 | A * | 11/2000 | Bishop ............... B01J 19/10 310/328 |
| 6,216,538 | B1 | 4/2001 | Yasuda et al. |
| 6,221,258 | B1 | 4/2001 | Feke et al. |
| 6,245,207 | B1 | 6/2001 | Yasuda et al. |
| 6,273,262 | B1 | 8/2001 | Yasuda et al. |
| 6,454,945 | B1 | 9/2002 | Weigl et al. |
| 6,719,449 | B1 | 4/2004 | Laugham, Jr. et al. |
| 6,881,314 | B1 | 4/2005 | Wang et al. |
| 6,929,750 | B2 | 8/2005 | Laurell et al. |
| 6,948,843 | B2 | 9/2005 | Laugham, Jr. et al. |
| 6,949,355 | B2 | 9/2005 | Yamanishi et al. |
| 7,198,813 | B2 | 4/2007 | Wixforth |
| 7,276,170 | B2 | 10/2007 | Oakey et al. |
| 7,329,039 | B2 | 2/2008 | Laugham, Jr. et al. |
| 7,398,685 | B2 | 7/2008 | Itoh et al. |
| 7,521,023 | B2 | 4/2009 | Laugham, Jr. et al. |
| 7,686,500 | B2 | 3/2010 | Laugham, Jr. et al. |
| 7,687,026 | B2 | 3/2010 | Laugham, Jr. et al. |
| 7,687,039 | B2 | 3/2010 | Laugham, Jr. et al. |
| 7,811,525 | B2 | 10/2010 | Laugham, Jr. et al. |
| 7,837,040 | B2 | 11/2010 | Ward et al. |
| 7,846,382 | B2 | 12/2010 | Strand et al. |
| 7,897,044 | B2 | 3/2011 | Hoyos et al. |
| 7,964,078 | B2 | 6/2011 | Lee et al. |
| 7,981,368 | B2 | 7/2011 | Laugham, Jr. et al. |
| 8,083,706 | B2 | 12/2011 | Leonard et al. |
| 8,134,705 | B2 | 3/2012 | Kaduchak et al. |
| 8,159,110 | B2 | 4/2012 | Tsuyoshi et al. |
| 8,263,005 | B2 | 9/2012 | Laugham, Jr. et al. |
| 8,266,950 | B2 | 9/2012 | Kaduchak et al. |
| 8,266,951 | B2 | 9/2012 | Kaduchak et al. |
| 8,273,302 | B2 * | 9/2012 | Takahashi ............ B01D 21/283 204/157.42 |
| 8,309,408 | B2 | 11/2012 | Ward et al. |
| 8,573,060 | B2 | 11/2013 | Huang et al. |
| 8,830,451 | B1 | 9/2014 | Graves et al. |
| 8,863,958 | B2 | 10/2014 | Kaduchak et al. |
| 8,932,520 | B2 | 1/2015 | Goddard et al. |
| 2006/0037915 | A1 * | 2/2006 | Strand ................. B01D 21/283 210/748.05 |
| 2006/0163166 | A1 | 7/2006 | Hawkes et al. |
| 2007/0267295 | A1 | 11/2007 | Chang et al. |
| 2008/0053787 | A1 | 3/2008 | Bagajewicz |
| 2008/0245709 | A1 | 10/2008 | Kaduchak et al. |
| 2008/0245745 | A1 | 10/2008 | Ward et al. |
| 2009/0042239 | A1 | 2/2009 | Ward et al. |
| 2009/0049917 | A1 * | 2/2009 | Beck .................... B01J 19/008 73/590 |
| 2009/0050573 | A1 | 2/2009 | Ward et al. |
| 2009/0053686 | A1 | 2/2009 | Ward et al. |
| 2009/0226994 | A1 | 9/2009 | Lemor et al. |
| 2010/0006501 | A1 | 1/2010 | Laurell et al. |
| 2010/0078384 | A1 | 4/2010 | Yang |
| 2010/0193407 | A1 | 8/2010 | Steinberg et al. |
| 2010/0323342 | A1 | 12/2010 | Gonzalez Gomez et al. |
| 2011/0024335 | A1 | 2/2011 | Ward et al. |
| 2011/0033922 | A1 | 2/2011 | Landers et al. |
| 2011/0154890 | A1 | 6/2011 | Holm et al. |
| 2011/0262990 | A1 | 10/2011 | Wang et al. |
| 2012/0028293 | A1 | 2/2012 | Wixforth et al. |
| 2012/0058546 | A1 | 3/2012 | Lee et al. |
| 2012/0088295 | A1 | 4/2012 | Yasuda et al. |
| 2012/0153185 | A1 | 6/2012 | Ito |
| 2012/0187209 | A1 | 7/2012 | Friend et al. |
| 2012/0298205 | A1 | 11/2012 | Schertzer et al. |
| 2013/0029407 | A1 | 1/2013 | Terazono et al. |
| 2013/0043170 | A1 | 2/2013 | Rose et al. |
| 2013/0048565 | A1 | 2/2013 | Fiering et al. |
| 2013/0101468 | A1 * | 4/2013 | Boutin ................. C02F 1/36 422/128 |
| 2013/0116459 | A1 | 5/2013 | Marrone et al. |
| 2013/0139575 | A1 | 6/2013 | Lee et al. |
| 2013/0175226 | A1 | 7/2013 | Coussios et al. |
| 2013/0192958 | A1 | 8/2013 | Ding et al. |
| 2013/0213488 | A1 | 8/2013 | Weitz et al. |
| 2013/0228530 | A1 | 9/2013 | Di Carlo et al. |
| 2013/0233059 | A1 | 9/2013 | McDonnell et al. |
| 2013/0284271 | A1 | 10/2013 | Lipkens et al. |
| 2013/0302213 | A1 | 11/2013 | Lipkens et al. |
| 2013/0330247 | A1 | 12/2013 | Wilson et al. |
| 2014/0008307 | A1 | 1/2014 | Guldiken et al. |
| 2014/0011240 | A1 | 1/2014 | Lipkens et al. |
| 2014/0033808 | A1 | 2/2014 | Ding et al. |
| 2014/0216992 | A1 | 8/2014 | Rose et al. |
| 2015/0111195 | A1 | 4/2015 | Hamman et al. |

FOREIGN PATENT DOCUMENTS

| | | | |
|---|---|---|---|
| WO | 02072236 | A1 | 9/2002 |
| WO | 03079006 | A1 | 9/2003 |
| WO | 2004079716 | A1 | 9/2004 |
| WO | 2008122051 | A1 | 10/2008 |
| WO | 2010123453 | A1 | 10/2010 |
| WO | 2011126892 | A2 | 10/2011 |
| WO | 2012027366 | A2 | 3/2012 |
| WO | 2012004076 | A1 | 8/2012 |
| WO | 2013048323 | A1 | 4/2013 |
| WO | 2014004630 | A1 | 1/2014 |
| WO | 2014055219 | A2 | 4/2014 |
| WO | 2014133451 | A1 | 9/2014 |
| WO | 2015009284 | A1 | 1/2015 |

* cited by examiner

SYSTEM FOR MANIPULATION AND SORTING OF PARTICLES

CROSS-REFERENCE TO RELATED APPLICATIONS

This application is a 371 National Stage Entry of PCT/US15/34836 filed on Jun. 9, 2015, which claims the benefit of and priority to U.S. Provisional Patent Application No. 62/009,550 filed on Jun. 9, 2014, and U.S. Provisional Patent Application No. 62/019,920 filed on Jul. 2, 2014, each of which is hereby incorporated by reference in its entirety.

FIELD OF THE INVENTION

The present invention is directed to systems and methods for manipulation and sorting of particles. More specifically, the present invention is directed to systems and methods for sound wave manipulation and sorting of particles, including the concentration, focusing, and characterization of particles, cells, and microorganisms using acoustic waves.

BACKGROUND OF THE INVENTION

Conventional particle manipulation methods are generally used to spatially compress a sample flow of particles, typically in two dimensions. Often, these particle manipulation methods have various problems. For example, many manipulation systems generate turbulent fluid flow during manipulation. The turbulent flow decreases manipulation effectiveness and process efficiency.

One method of decreasing turbulent flow includes the use of constrictors or spiraling configurations. However, these configurations suffer from decreased efficiency and increased cost. Additionally, particle manipulation generates heat, which may damage certain fluids as well as components of the particle manipulation system. As such, increases in temperature are currently limiting on the use and effectiveness of existing particle manipulation systems.

A system that shows one or more improvements in comparison to the prior art would be desirable in the art.

BRIEF DESCRIPTION OF THE INVENTION

In an embodiment, a manipulation system includes a flow chamber arranged and disposed to receive a fluid containing a particulate and provide in-line sound wave manipulation of at least a portion of the particulate from the fluid, and a transducer positioned to facilitate the in-line sound wave manipulation within the flow chamber. The flow chamber includes at least a first portion and a second portion, the first portion being self-aligned and secured to the second portion.

In another embodiment, a sound manipulation system includes a flow chamber arranged and disposed to receive a fluid containing a particulate and provide in-line sound wave manipulation of at least a portion of the particulate from the fluid, a transducer positioned to facilitate the in-line sound wave manipulation within the flow chamber, and a bubble-removing mechanism.

In another embodiment, a manipulation system includes a flow chamber arranged to receive a fluid containing a particulate and disposed for in-line acoustic manipulation of at least a portion of the particulate from the fluid, a transducer positioned to facilitate the in-line acoustic manipulation within the flow chamber, and at least one sensor arranged and disposed to measure a property of an article selected from the group consisting of the fluid, the particulate, the transducer, and combinations thereof.

In another embodiment, a manipulation system includes a flow chamber arranged and disposed to receive a fluid containing a particulate and provide in-line sound wave manipulation of at least a portion of the particulate from the fluid, a transducer positioned to facilitate the in-line sound wave manipulation within the flow chamber, and a passive thermal transfer arrangement positioned to transfer heat from the transducer during the in-line sound wave manipulation.

In another embodiment, a manipulation system includes a flow chamber arranged to receive a fluid containing a particulate and disposed for in-line sound wave manipulation of at least a portion of the particulate from the fluid, a transducer detachably secured to the flow chamber, the transducer being positioned to at least partially facilitate the in-line sound wave manipulation within the flow chamber, and an information storage device operably connected to the flow chamber, the information storage device being arranged and disposed to adjust the in-line sound wave manipulation in response to parameters selected from the group consisting of resonant frequency of the transducer, bandwidth of the transducer, electrical impedance of the transducer, capacitance of the transducer, resonant frequency of the flow chamber, flow rates of the fluid within the flow chamber, temperature of the transducer, power of the transducer, operational life information of the transducer, and combinations thereof. The information storage device sets an initial configuration of the transducer upon securing the transducer to the flow chamber, the initial configuration of the transducer corresponding to the dimensions of the flow chamber.

In another embodiment, a separation system includes a flow chamber arranged and disposed to provide laminar flow of at least a first fluid and a second fluid, and to provide in-line sound wave separation of at least a portion of a particulate from the first fluid, a first inlet configured to provide the first fluid to the flow chamber, a second inlet configured to provide the second fluid to the flow chamber, the second inlet being parallel or substantially parallel to the first inlet, a first outlet configured to receive the first fluid, a second outlet configured to receive the second fluid containing at least a portion of the particulate, and a divider oriented perpendicular or substantially perpendicular to the direction of gravity and positioned to at least partially separate the first fluid and the second fluid within a portion of the flow chamber.

In another embodiment, a manipulation system includes a flow chamber arranged to receive a fluid containing a particulate and disposed for in-line sound wave manipulation of at least a portion of the particulate from the fluid, and a transducer positioned to facilitate the in-line sound wave manipulation within the flow chamber. The flow chamber includes at least a first portion and a second portion, the first portion being self-aligned and secured to the second portion.

In another embodiment, a manipulation system includes a disposable flow chamber arranged to receive a fluid containing a particulate and disposed for in-line sound wave manipulation of at least a portion of the particulate from the fluid, and a transducer positioned to facilitate the in-line sound wave manipulation within the flow chamber. The transducer is detachable from the disposable flow chamber and reusable.

In another embodiment, a manipulation system includes a flow chamber arranged to receive a fluid containing a particulate and disposed for in-line sound wave manipulation of at least a portion of the particulate from the fluid, and a transducer positioned to facilitate the in-line sound wave manipulation within the flow chamber. The flow chamber is manufactured with injection molding, chemical etching, CNC machining, vacuum molding, other mass-production methods, or a combination thereof.

In another embodiment, a manipulation system includes a flow chamber arranged to receive a fluid containing a particulate and disposed for in-line sound wave manipulation of at least a portion of the particulate from the fluid, a transducer positioned to facilitate the in-line sound wave manipulation within the flow chamber, and at least two acoustic impedance layers positioned with respect to the flow chamber and the transducer to enhance the in-line acoustic manipulation. The acoustic impedance layer is formed from at least one material selected from the group consisting of polymer, metal, ceramic, glass, silicon, and a combination thereof.

In another embodiment, a manipulation system includes a flow chamber arranged to receive a fluid containing a particulate and disposed for in-line sound wave manipulation of at least a portion of the particulate from the fluid, a transducer positioned to facilitate the in-line sound wave manipulation within the flow chamber, and a fluid delivery system operably connected to the flow chamber, the fluid delivery system being arranged and disposed to automatically control the fluid delivery provided from the fluid delivery system to the flow chamber, to control the flow sequence, flow rate, flow time span, fluid composition, and combinations thereof.

In another embodiment, a manipulation system includes a flow chamber arranged to receive a first fluid containing a particulate and a second fluid, and disposed for in-line sound wave manipulation of at least a portion of the particulate from the first fluid, and a transducer positioned to facilitate the in-line sound wave manipulation within the flow chamber. The first fluid is initially located at an acoustic pressure node and has an equal or relatively higher acoustic impedance as compared to the second fluid, and the second fluid is initially located at an acoustic pressure antinode and has an equal or relatively lower acoustic impedance as compared to the first fluid.

In another embodiment, a manipulation system includes a flow chamber arranged to receive a fluid containing a particulate and disposed for in-line sound wave manipulation of at least a portion of the particulate from the fluid, and a transducer arrangement including an orthogonal arrangement of a plurality of piezoelectric devices, the transducer arrangement being positioned to facilitate the in-line sound wave manipulation within the flow chamber.

In another embodiment, a manipulation system includes a flow chamber arranged to receive a fluid containing a particulate and disposed for in-line sound wave manipulation of at least a portion of the particulate from the fluid, and a transducer positioned to facilitate the in-line sound wave manipulation within the flow chamber. The flow chamber facilitates generation of multiple parallel flows with at least two fluid compositions within the flow chamber.

In another embodiment, a manipulation system includes a flow chamber arranged to receive a fluid containing a particulate and disposed for in-line sound wave manipulation of at least a portion of the particulate from the fluid, a transducer positioned to facilitate the in-line sound wave manipulation within the flow chamber, and an electrical matching circuit arranged and disposed to suppress frequencies outside of a select bandwidth capable of being used by the transducer to provide the sound waves.

In another embodiment, a manipulation system includes a flow chamber arranged to receive a fluid containing a particulate and disposed for in-line sound wave manipulation of at least a portion of the particulate from the fluid, and a transducer positioned to provide sound waves to the flow chamber for the in-line sound wave manipulation, the transducer being driven by at least one of a pulse-width-modulation drive and a square wave drive.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are systems and methods for sound wave manipulation and sorting of particles. Embodiments of the present disclosure, for example, in comparison to concepts failing to include one or more of the features disclosed herein, provide disposable flow chambers, provide detachable sound wave manipulation transducers, provide reusable sound wave manipulation transducers, facilitates bubble removal, increases laminar flow, increases parallel flow, increases transducer protection, provides flow measurement with a transducer, provides stored transducer calibration information, provides passive thermal transfer from the transducer, provides composite piezoelectric transducers, or a combination thereof.

Figure 1:
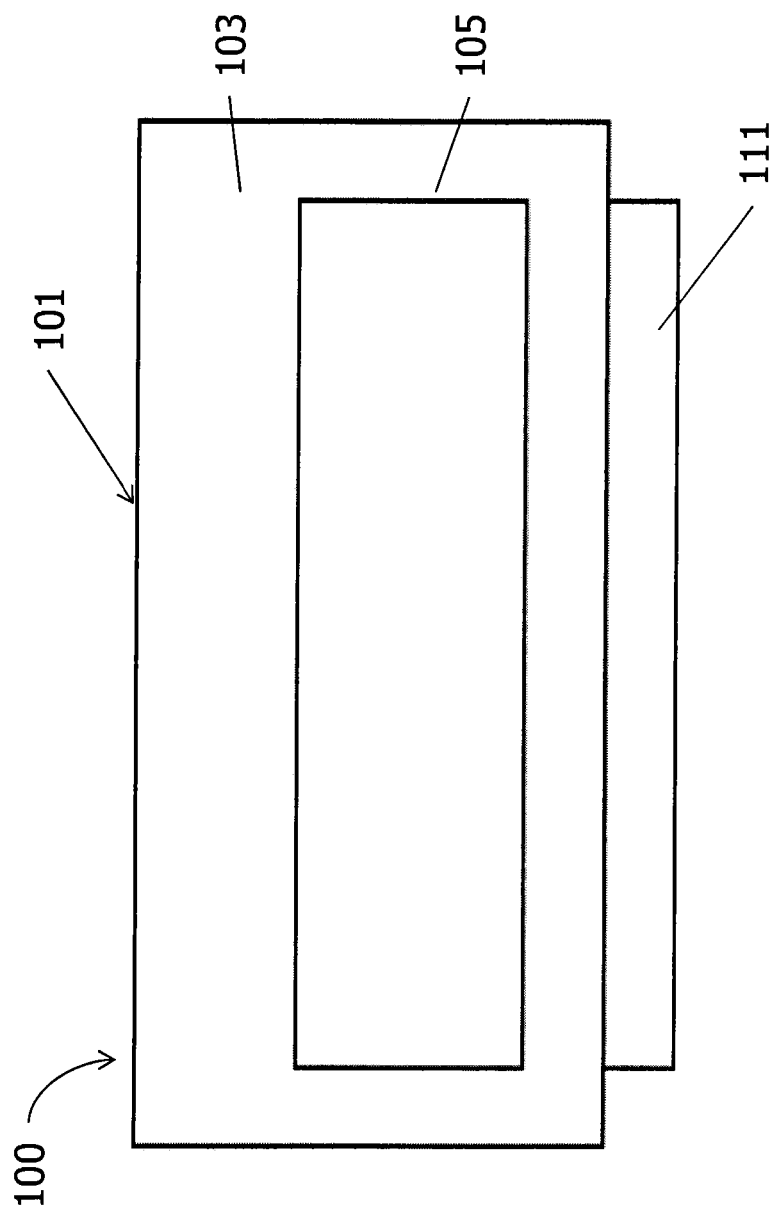
FIG. 1 shows a section view of a system, according to an embodiment of the disclosure.

Referring to FIG. 1, a system 100 includes a flow chamber 101 and a transducer 111. The flow chamber 101 is configured to facilitate flow of at least one fluid therethrough. The transducer 111 is positioned relative to the flow chamber 101 to facilitate in-line sound wave manipulation of the at least one fluid flowing through the flow chamber 101. For example, in one embodiment, the transducer 111 is secured to the flow chamber 101 and configured to direct sound waves towards the fluid within the flow chamber 101. The sound waves pass through the at least one fluid in the flow chamber 101, manipulating at least one particle within the at least one fluid such as, for example, by sorting the at least one particle, separating the at least one particle from one or more fluids, or a combination thereof. As used herein, the term "sound wave" includes infrasound waves, acoustic waves, and/or ultrasound waves. Infrasound waves include sound pressure waves having a frequency below the lower limit of the normal human hearing range, which is about 20 hertz (Hz). Acoustic waves include sound pressure waves having a frequency within the human hearing range, which is between about 20 Hz and about 20 kHz. Ultrasound waves include sound pressure waves having a frequency above the upper limit of the normal human hearing range, which is about 20 kHz.

In one embodiment, the transducer 111 includes a composite piezoelectric transducer having at least one piezoelectric transducer in a matrix material. For example, in another embodiment the composite piezoelectric transducer includes one or more ceramic piezoelectric transducers positioned in a polymer matrix. In a further embodiment, ceramic and polymer composite configurations of the composite piezoelectric transducer include, but are not limited to, 2-2, 0(0)-3, 1(0)-3, 2(0)-2-2. Other suitable transducers include any transducer that generates sound waves, such as but not limited to, a resonator, an interdigitated transducer (IDT), a surface acoustic wave (SAW) device, a standing surface acoustic wave (SSAW) device, a bulk resonator, a thin-film bulk acoustic resonator, a microelectromechanical system (MEMS), an electromagnetic acoustic transducer, or a combination thereof. As will be appreciated by those skilled in the art, the SAW device is not limited to any one configuration, and may include any suitable configuration, such as, but not limited to, interdigitated electrodes on a piezo substrate, interdigitated electrodes on a piezo film deposited on a non-piezo substrate, a wedge transducer (see FIG. 16) on a non-piezo substrate, a comb transducer on a non-piezo substrate, or a combination thereof. Suitable piezo substrates include, for example, quartz and/or lithium niobate, while suitable non-piezo substrates include, for example, glass and/or pyrex.

Figure 17:
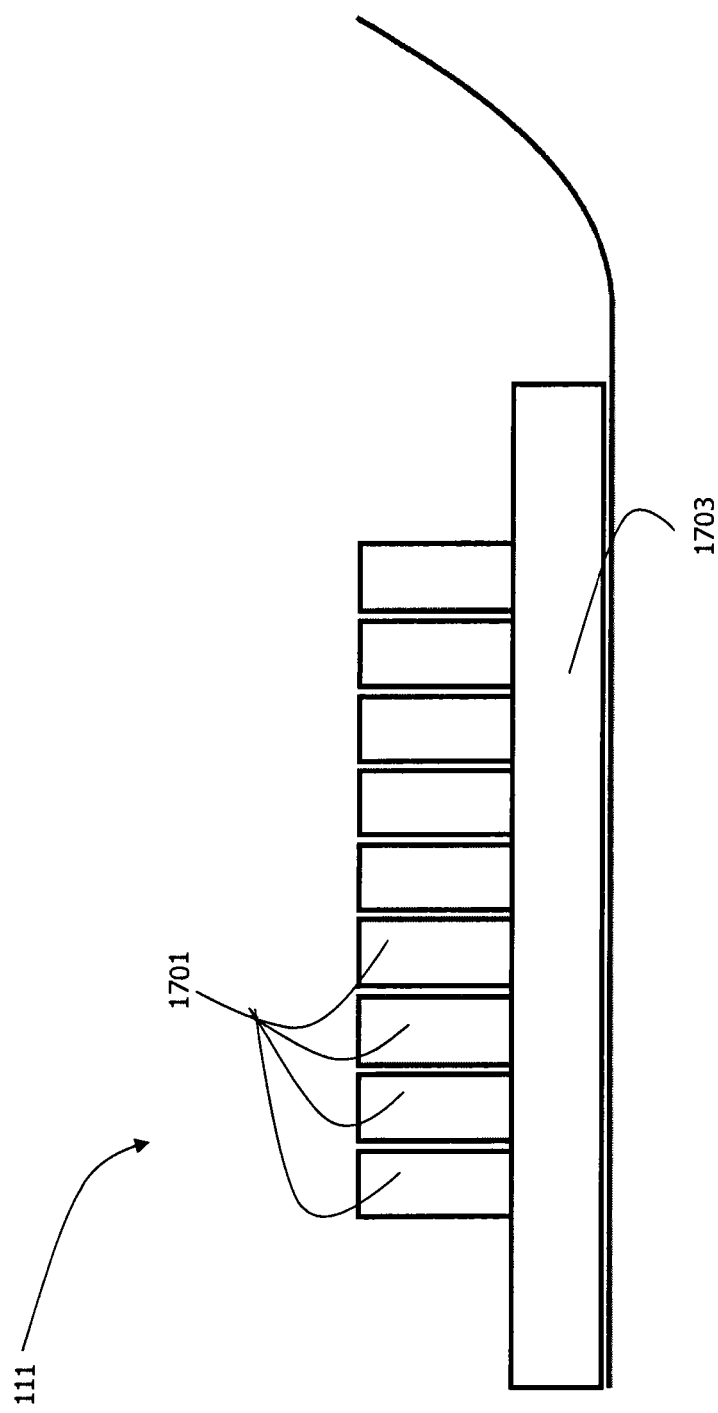
FIG. 17 shows a section view of an orthogonal arrangement of transducers elements, according to an embodiment of the disclosure.

Additionally or alternatively, as illustrated in FIG. 17, the transducer 111 includes a plurality of piezoelectric devices 1701. The plurality of piezoelectric devices 1701 are positioned to form an orthogonal arrangement, forming a plurality of transducer posts for generating pressure waves. In another embodiment, the plurality of piezoelectric devices 1701 are secured to an electrically conductive matching layer 1703, such as, but not limited to, a chamber component or part of a chamber component plated with a conductive metal. The plurality of piezoelectric devices 1701 are secured by any suitable means, including, for example, bonding and/or casting. In a further embodiment, a surface of the plurality of piezoelectric devices 1701 not secured to the matching layer 1703 is secured to a foil or flex circuit to provide electrical conductivity thereof. Additionally or alternatively, top and bottom electrodes of the plurality of piezoelectric devices 1701 are electrically connected by bonding a conductive metal foil or flexible circuit to the electrodes, facilitating formation of a 2-2 arrangement of transducer elements.

A method of forming the transducer 111 including the plurality of piezoelectric devices 1701 includes, but is not limited to, providing a single monolithic transducer with electrodes on both upper and lower surface thereof, securing the monolithic transducer to the electrically conductive matching layer 1703, and cutting the monolithic transducer into a matrix of individual transducer rods or strips. The matrix of individual transducer rods or strips form the plurality of piezoelectric devices 1701. Additionally, air kerfs between the plurality of piezoelectric devices 1701 provide increased thickness resonance of the material, which increases operating efficiency of the transducer 111.

Figure 2:
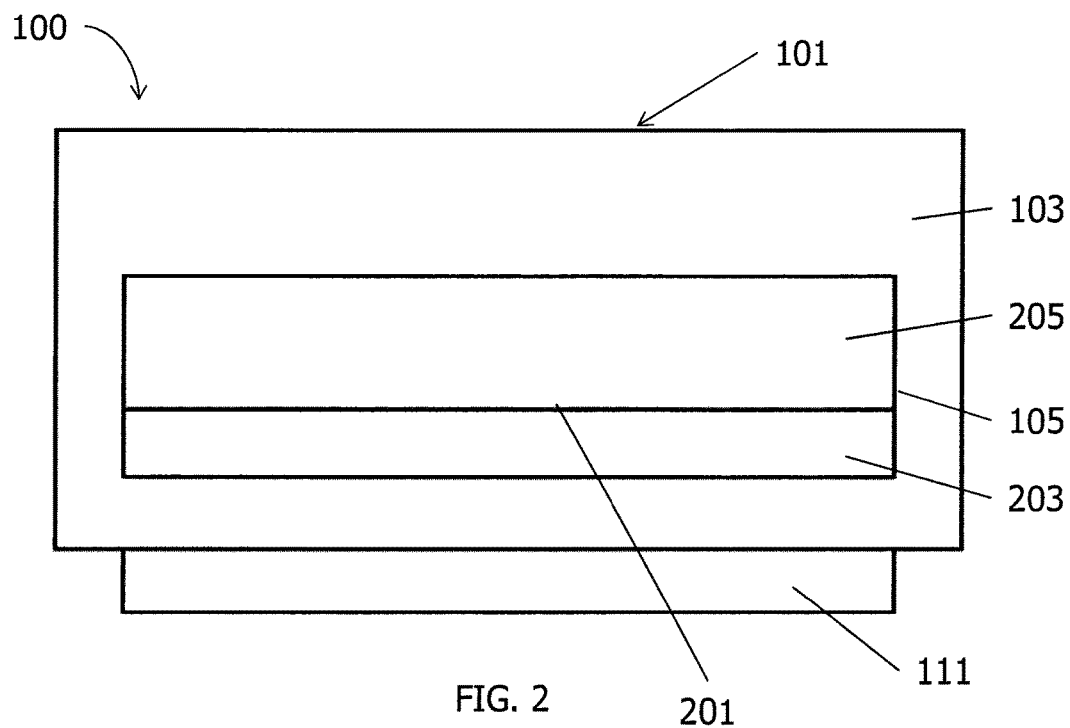
FIG. 2 shows a section view of a flow chamber including a divider, according to an embodiment of the disclosure.
Figure 3:
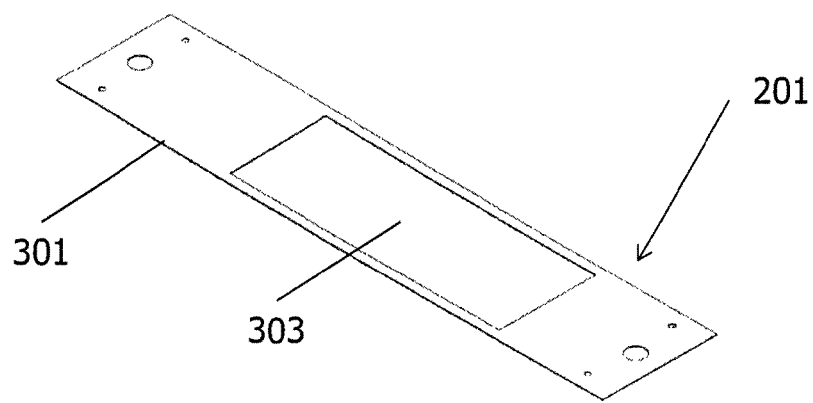
FIG. 3 shows a perspective view of a divider, according to an embodiment of the disclosure.

Returning to FIG. 1, the flow chamber 101 includes a chamber body 103 having a fluid receiving portion 105 formed therein. In one embodiment, the flow chamber 101 is configured to facilitate laminar or substantially laminar flow of the at least one fluid therethrough. Additionally or alternatively, as illustrated in FIGS. 2-3, the flow chamber 101 includes a divider 201 positioned within the fluid receiving portion 105. The divider 201 is oriented to at least partially separate a first fluid 203 and a second fluid 205 within the fluid receiving portion 105. For example, referring to FIG. 3, the divider 201 includes a divider body 301 having an opening 303 formed therein. The divider body 301 separates the first fluid 203 and the second fluid 205 entering and/or exiting the fluid receiving portion 105, while the opening 303 permits contact between the first fluid 203 and the second fluid 205 as they flow through the receiving portion 105. By separating the first fluid 203 and the second fluid 205 entering the receiving portion 105, the divider 201 facilitates laminar flow of the first fluid 203 and the second fluid 205, decreases or eliminates turbulent flow, decreases or eliminates mixing of the first fluid 203 and the second fluid 205, or a combination thereof.

The flow chamber 101 and/or the divider 201 are formed from the same, substantially the same, or different materials, and include any suitable material for contacting the at least one fluid provided to the fluid receiving portion 105. Suitable materials include, but are not limited to, acrylics, polycarbonates, polypropylenes, polyvinylidene fluoride (PVDF), polytetrafluoroethylene (PTFE), other plastics, stainless steel, thermally conductive metal, aluminum, metal alloys, other alloys, other metals, low durometer silicone, low durometer urethane, or a combination thereof. Additionally, the flow chamber 101 and/or the divider 201 are formed using the same, substantially the same, or difference processes, such as, but not limited to, laser cutting, waterjet cutting, injection molding, chemical etching, computer numeric control (CNC) machining, vacuum molding, stamping, die stamping, or a combination thereof. For example, in one embodiment, the flow chamber 101 includes plastic formed using injection molding, and the divider 201 includes thermally conductive metal formed through cutting and/or stamping. In another embodiment, the plastic material of the flow chamber 101 and the thermally conductive metal of the divider 201 are secured to each other using a thermal process. In a further embodiment, the thermal process includes heating the divider 201 to the fusion point of the plastic chamber components by, for example, eddy current heat, electrical resistive heating, and/or direct thermal contact.

Figure 4:
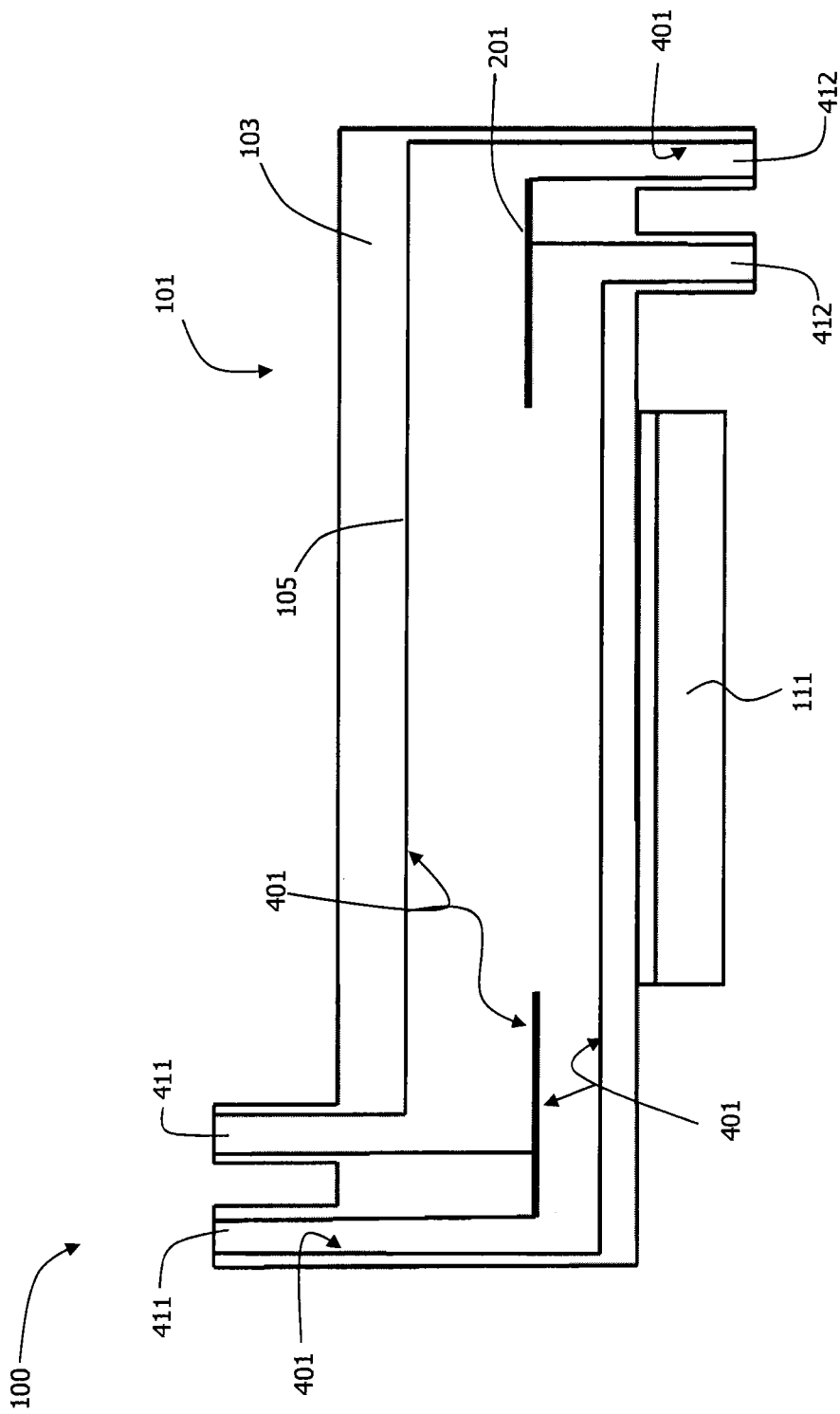
FIG. 4 shows a section view of a flow chamber including a bubble reducing element, according to an embodiment of the disclosure.

Turning to FIG. 4, in one embodiment, the flow chamber 101 includes a bubble reducing element 401. In another embodiment, the bubble reducing element 401 is provided on at least one surface of the flow receiving portion 105, at least one surface of the divider 201, or a combination thereof. In a further embodiment, the bubble reducing element 401 is provided on a surface of a fluid inlet 411 and/or a fluid outlet 412 extending from the chamber body 103. The bubble reducing element 401 includes any suitable element configured to reduce or eliminate attachment of air bubbles to fluid contacting surfaces of the system 100. One suitable bubble reducing element 401 includes a hydrophilic surface and/or coating such as, but not limited to, a titanium dioxide ($TiO_2$) coating. Another suitable bubble reducing element 401 includes a surface coated with an organic compound, such as Parylene C, and plasma treated to form a hydrophilic, blood compatible surface. Additionally or alternatively, the bubble reducing element 401 includes a physical structure capable of reducing or eliminating attachment of air bubbles. Suitable physical structures include, for example, grooves, bumps, scales, or a combination thereof. By reducing or eliminating the attachment of air bubbles to the fluid contacting surfaces of the system 100, the bubble reducing element 401 increases laminar flow of the fluid in the fluid receiving portion 105.

Figure 5:
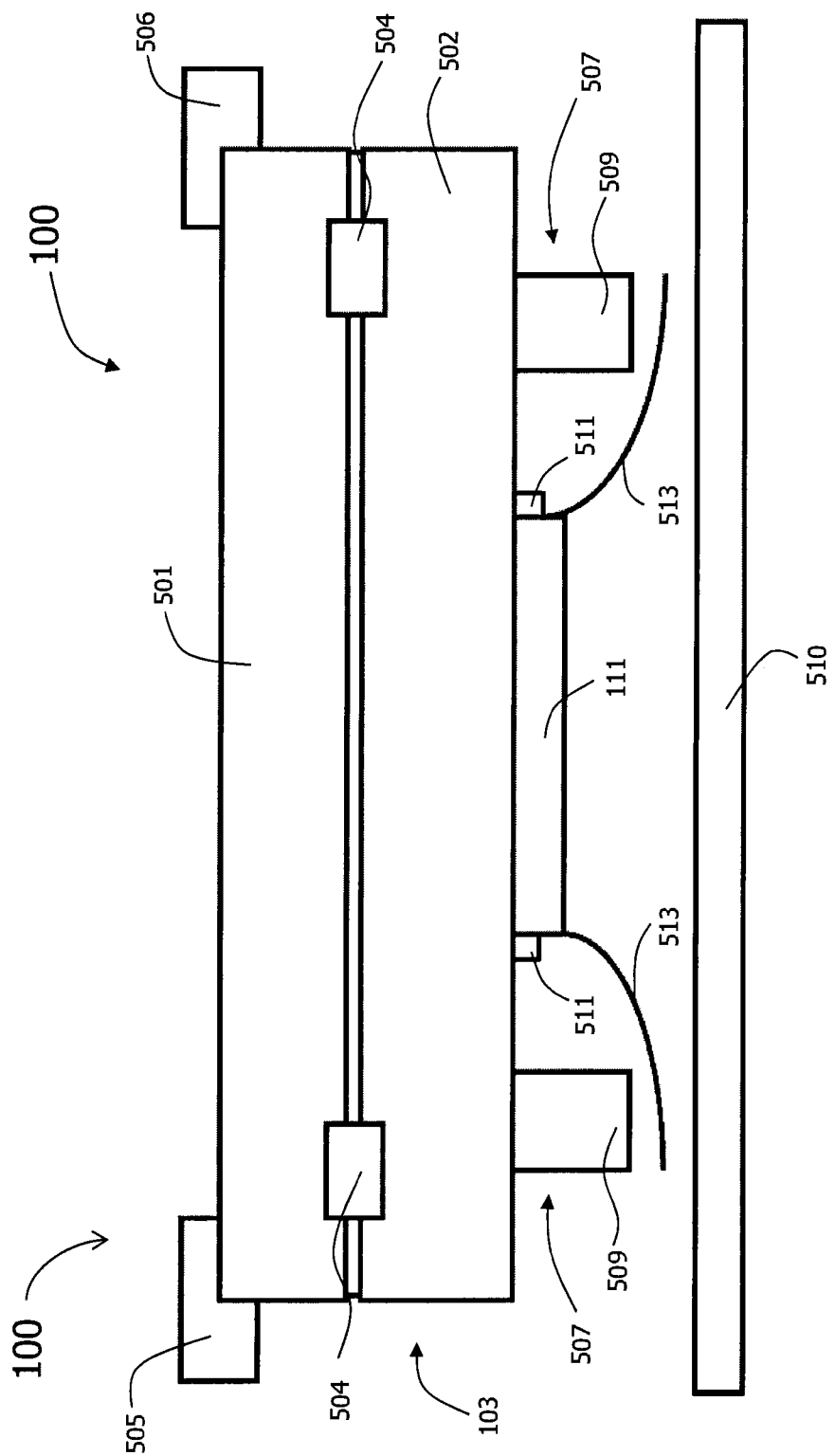
FIG. 5 shows a front view of a system, according to an embodiment of the disclosure.

Referring to FIG. 5, in one embodiment, the flow chamber 101 includes one or more features formed therein and/or extending therefrom. In another embodiment, the features include a first portion 501 and a second portion 502, the first portion 501 and the second portion 502 being secured together to form the chamber body 103 and/or the fluid receiving portion 105. The first portion 501, the second portion 502, and/or the divider 201 are secured with any suitable securing agent or process. One suitable securing agent includes an adhesive or sealant. Certain adhesives or sealants, such as, but not limited to, florescent adhesives and/or opaque adhesives are used to both secure the features of the flow chamber 101 and test the seal between the features of the flow chamber 101. Other suitable securing agents include a pressure sensitive adhesive, a gasket seal, any other agent that decreases or eliminates adhesive cure time, or a combination thereof. Suitable securing processes include, but are not limited to, thermal plastic welding, induction welding, or a combination thereof.

Additionally or alternatively, the first portion 501, the second portion 502, and/or the divider 201 include one or more alignment features 504 (see FIG. 3 for alignment features of the divider 201, which is not shown in FIG. 5).

In one embodiment, the one or more alignment features 504 align the first portion 501, the second portion 502, and/or the divider 201, and the securing agent and/or process secures the first portion 501, the second portion 502, and/or the divider 201. In another embodiment, the one or more alignment features 504 align and at least partially secure the first portion 501, the second portion 502, and/or the divider 201. Suitable alignment features 504 include, but are not limited to, clamping features, corresponding projections and recesses, overlapping portions, posts and corresponding apertures, or a combination thereof.

Other features of the flow chamber 101 include, but are not limited to, at least one inlet feature 505 and/or at least one outlet feature 506. For example, in one embodiment, the first portion 501 and/or the second portion 502 includes the at least one inlet feature 505 and/or the at least one outlet feature 506 formed therein and/or extending therefrom. The inlet feature 505 and the outlet feature 506 fluidly connect the fluid receiving section 105 with an exterior of the flow chamber 101, facilitating flow of at least one fluid into and out of the fluid receiving section 105. Suitable inlet features 505 and/or outlet features 506 include, but are not limited to, molded tubing connections, barbs, or a combination thereof.

In one embodiment, as illustrated in FIG. 5, the second portion 502 includes a transducer receiving portion 511 formed therein and/or extending therefrom. The transducer receiving portion 511 is configured to receive the transducer 111, orient the transducer 111 with respect to the flow chamber 101, and/or secure the transducer 111 to the flow chamber 101. For example, in another embodiment, the transducer 111 is integrally or detachably secured within the transducer receiving portion 511. In a further embodiment, the transducer receiving portion 511 is configured to set a distance between the transducer 111 and the chamber body 103, forming a matching layer between the transducer 111 and the fluid receiving portion 105. As will be appreciated by those skilled in the art, securing of the transducer to the flow chamber 101 is not limited to the embodiment above, and additionally or alternatively includes the transducer receiving portion 511 formed in and/or on the first portion 501, the transducer 111 detachably secured directly to the flow chamber 101, the transducer 111 integrally secured to the flow chamber 101, or a combination thereof.

In addition to being secured to the flow chamber 101, the transducer 111 is electrically coupled to the system 100, such as, for example, to a system interface 510. Suitable system interfaces 510 include, for example, matching layers, such as, but not limited to, glass, silicon, ceramic, metal, polymer, any other suitable material for acoustic impedance matching, or a combination thereof. In one embodiment, the transducer 111 is soldered or otherwise thermally joined to the system interface 510, the thermally joining of the transducer 111 to the system interface 510 providing an electrical interface between the transducer 111 and the system interface 510. Alternatively, the transducer 111 is electrically coupled to the system interface 510 without thermal joining, such as, for example, through electrical interface elements 513. Suitable electrical interface elements 513 include, but are not limited to, foil, flex circuits, wire leads, metallic spring contacts, or a combination thereof.

The electrical interface elements 513 are configured to contact the system interface 510, the contact between the electrical interface elements 513 and the system interface 510 providing electrical communication between the transducer 111 and the system interface 510. For example, in one embodiment, the second portion 502 and/or any other portion of the flow chamber 101 includes a support feature 507, such as, but not limited to, a plurality of legs 509, standoffs, or a combination thereof. In another embodiment, the support feature 507 aligns the flow chamber 101 with and/or secures the flow chamber 101 to the system interface 510. In a further embodiment, the support feature 507 clamps the electrical interface elements 513 to the system interface 510, securing the electrical interface elements 513 to the system interface 510 and maintaining electrical communication therebetween. Alternatively, the securing of the flow chamber 101 to the system interface 510 positions the metallic spring contacts in contact with the system interface 510, providing electrical communication between the transducer 111 and the system interface 510.

Figure 18:
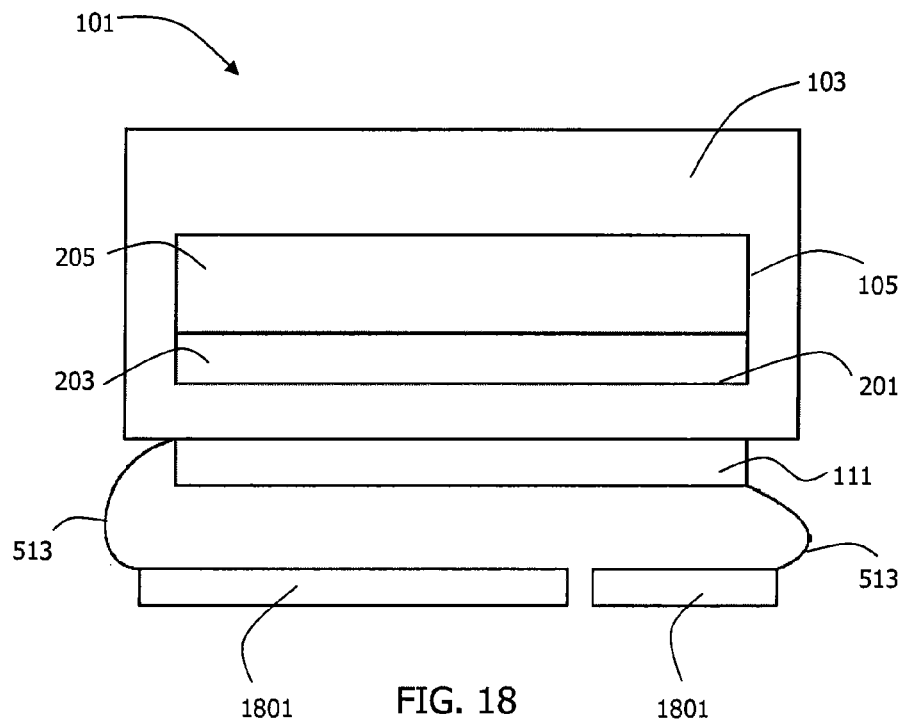
FIG. 18 shows a section view of a thermal transfer arrangement, according to an embodiment of the disclosure.
Figure 19:
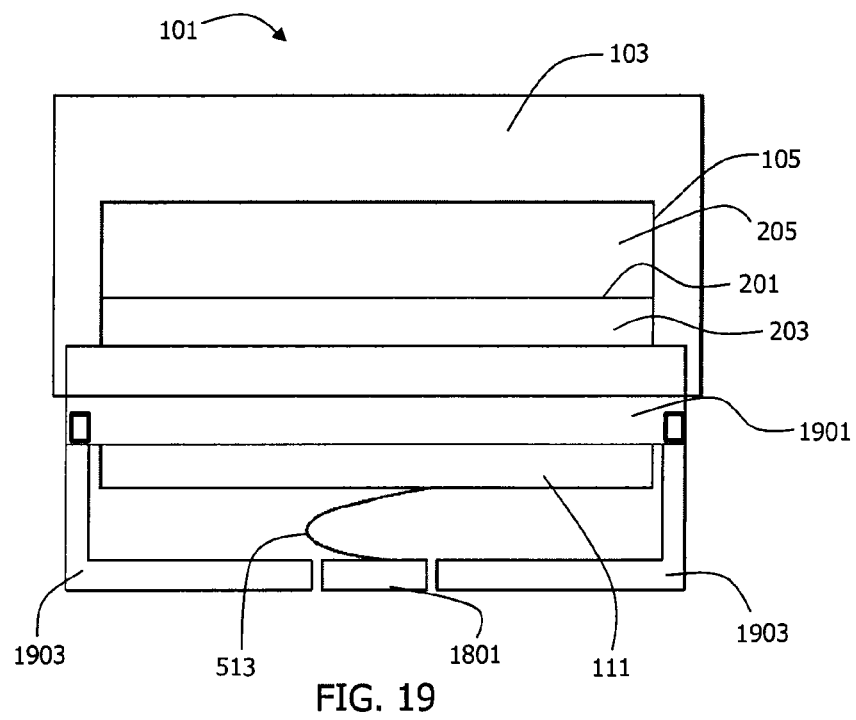
FIG. 19 shows a section view of an alternate thermal transfer arrangement, according to an embodiment of the disclosure.

Additionally or alternatively, the transducer 111 is cooled through passive thermal transfer. As used herein, the term "passive thermal transfer" includes any thermal transfer that does not require active circuitry or devices. In one embodiment, the electrical interface elements 513 are thermally conductive, providing both electrical communication and thermal transfer. For example, as illustrated in FIGS. 18-19, the electrical interface elements 513 are coupled to one or more conductive articles 1801, such as, but not limited to, cooling plates and/or heat sinks. The heat produced by the transducer 111 during use is transferred to the one or more conductive articles 1801 through the electrical interface elements 513, cooling the transducer 111 through passive thermal transfer. In another embodiment, the transducer 111 is secured directly to a thermally conductive material, such as, but not limited to, a thermally and/or electrically conductive matching layer 1901. In a further embodiment, a thermally and/or electrically conductive frame 1903 is couple to the thermally and/or electrically conductive matching layer 1901. The heat produced by the transducer 111 during use is transferred to the thermally and/or electrically conductive frame 1903 and/or the one or more conductive articles 1801 through the thermally and/or electrically conductive matching layer 1901 and/or the electrical interface elements 513, cooling the transducer 111 through passive thermal transfer. The cooling of the transducer 111 increases operational lifetime of the transducer, increases operating efficiency, decreases thermal damage to the transducer 111, the flow chamber 101, and/or the fluid within the fluid receiving portion 105, or a combination thereof. In an alternate embodiment, the transducer 111 is actively cooled, such as, for example, through an actively cooled frame or cooling article.

Figure 6:
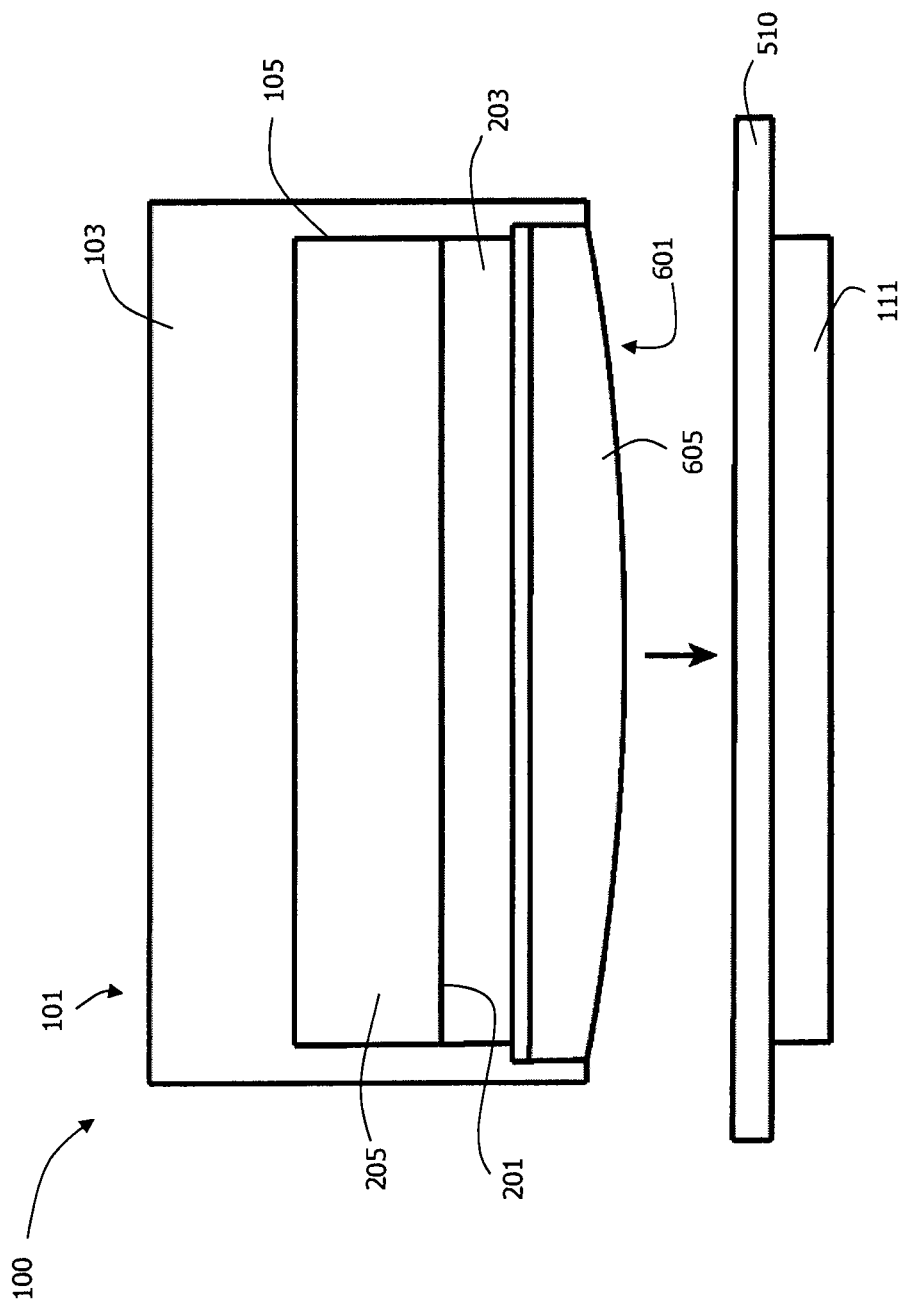
FIG. 6 shows a process view of a transducer being secured to a flow chamber, according to an embodiment of the disclosure.

Referring to FIG. 6, in an alternate embodiment, the system interface 510 is secured directly to the transducer 111 and/or positioned between the transducer 111 and the flow chamber 101. In another embodiment, the system 100 includes one or more intermediate members 601 positioned between the transducer 111 and the fluid receiving portion 105. In a further embodiment, the intermediate member 601 includes a couplant 605, such as, but not limited to, a low durometer polymeric interface attached to and/or positioned at least partially within the flow chamber 101. The low durometer polymeric interface forms an acoustic interface for the transducer 111. Additionally, the polymeric interface may include a covering, such as, but not limited to, a peel off covering configured to reduce or eliminate contamination of the polymeric interface.

Figure 7:
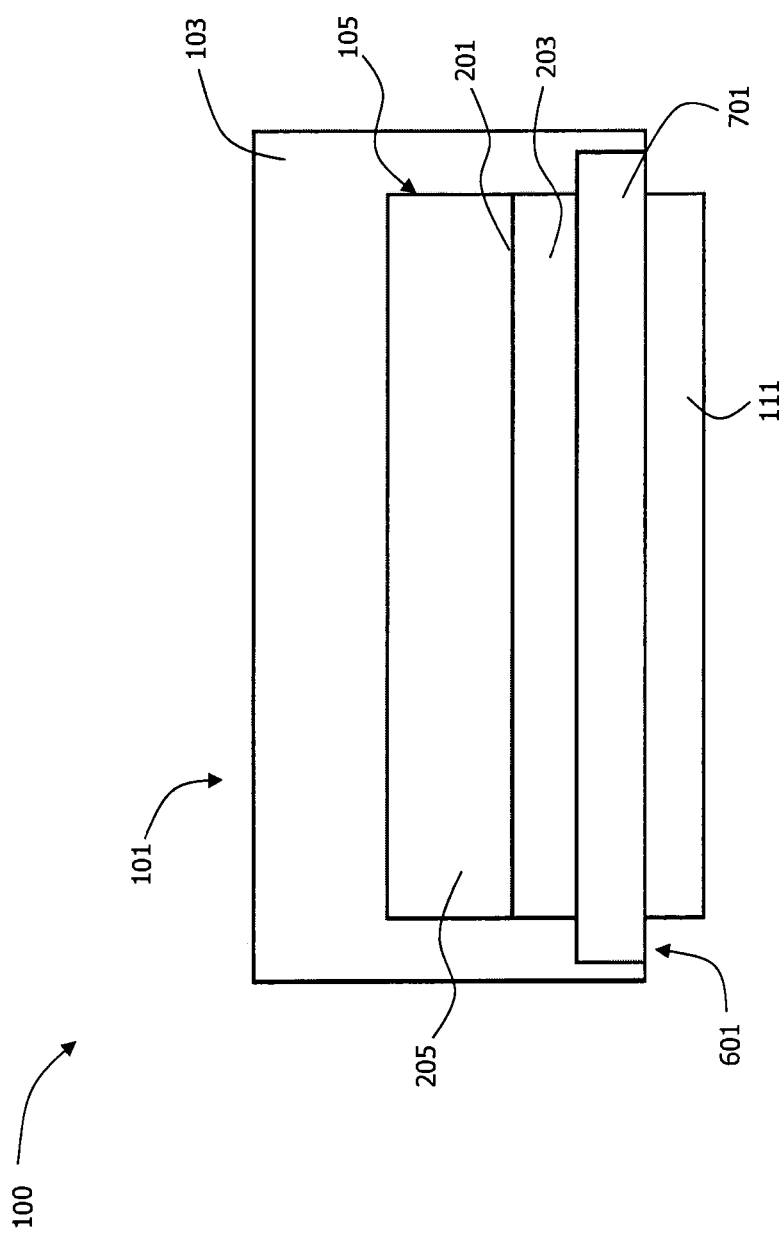
FIG. 7 shows a section view of a system including a matching layer, according to an embodiment of the disclosure.

In one embodiment, as illustrated in FIG. 7, the intermediate member 601 includes an acoustic matching layer 701. The acoustic matching layer 701 includes any suitable material secured to and/or positioned at least partially within the flow chamber 101, between the transducer 111 and the fluid receiving portion 105. Suitable materials are the same as or different from the materials of the flow chamber 103, and include, but are not limited to, poly(methyl methacrylate) (PMMA), PVDF, glass, silicon, ceramic, metal, polymer, any other material having an acoustic impedance equal to or between that of the transducer 111 and the fluid within the fluid receiving portion 105, or a combination thereof. For example, in another embodiment, the impedances from the transducer 111 to the acoustic matching layer 701 to the first fluid 203 within the fluid receiving portion 105 follow a geometric progression having the following equation:

$$Z(middle) = sqrt(Z(outside) * Z(inside)) \qquad \text{Equation 1:}$$

where Z is the acoustic impedance in MRayl. In a further embodiment, the acoustic matching layer 701 includes a thickness within a quarter-wavelength enhancing range, the quarter-wavelength enhancing range being defined by the equation:

$$N/2 * lambda + lambda/4 \qquad \text{Equation 2:}$$

where lambda is the wavelength of the transducer frequency in chamber body 103 or the fluid within the fluid receiving portion 105, and N is an integer corresponding to the number of half wavelengths fitting between the nodes.

As will be appreciated by those skilled in the art, the acoustic matching layer 701 is not limited to the impedance or thickness described in the example above, and may include any other suitable impedance and/or thickness. Other suitable impedances include, but are not limited to, any other geometric progression, a linear or arithmetic progression, and/or a harmonic progression. Other suitable thicknesses include, but are not limited to, any thickness outside the quarter-wavelength enhancing range.

The thickness of the acoustic matching layer 701 is formed by any suitable method, such as, for example, casting an acoustic matching material onto the transducer 111 and/or the flow chamber 101, grinding the acoustic matching material to the desired thickness, bonding layers of the acoustic matching material to the transducer 111 and/or the flow chamber 101, spray deposition of the acoustic matching material, or a combination thereof. Forming the acoustic matching layer 701 having a thickness within the quarter-wavelength enhancing range generates a single acoustic pressure node in the middle plane of the fluid receiving portion 105, which increases acoustic separation efficiency. Additionally or alternatively, the thickness of the acoustic matching layer 701 provides an optimized resonant frequency match between the transducer 111 and the dimensions of the flow chamber 101, provides an optimized acoustic impedance match between the fluid within the fluid receiving portion 105 and the transducer 111, or a combination thereof.

Figure 8:
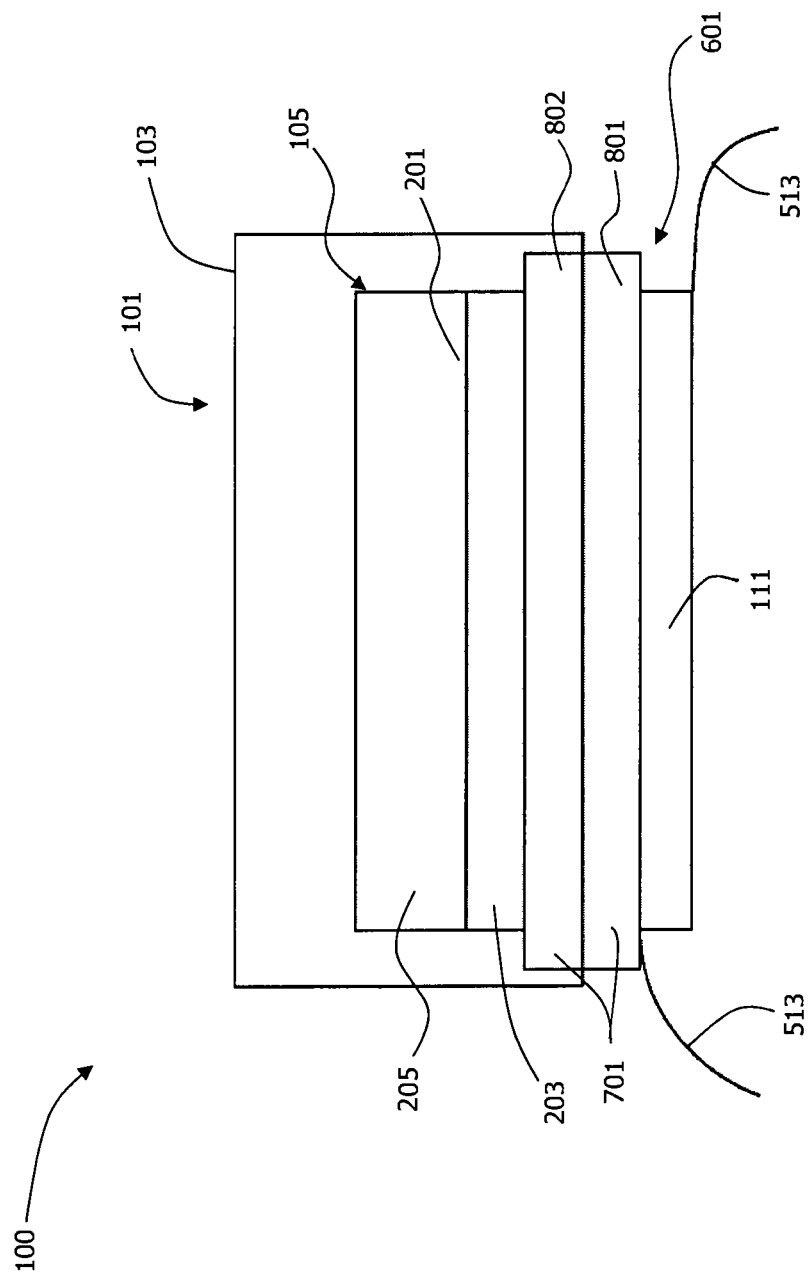
FIG. 8 shows a section view of a system including multiple matching layers, according to an embodiment of the disclosure.

Turning to FIG. 8, in one embodiment, the intermediate member 601 includes two or more of the acoustic matching layers 701, each of the two or more acoustic matching layers 701 having a material that is the same as or different from the material of the flow chamber 101. Suitable materials include, but are not limited to, polymer, metal, ceramic, glass, silicon, or combinations thereof. In another embodiment, each of the acoustic matching layers 701 includes a different acoustic impedance as compared to the transducer 111 and/or the other acoustic matching layer(s) 701, the two or more acoustic matching layers 701 forming an impedance gradient. For example, in a further embodiment, the transducer 111 includes an acoustic impedance of 25 MRayl, the two or more acoustic matching layers 701 include a first matching layer 801 having an impedance of 10 MRayl and a second matching layer 802 having an impedance of 4

MRayl, and the first fluid 203 includes an impedance of 1.6 MRayl. In the above example, each of the first matching layer 801 and the second matching layer 802 has a thickness within the quarter-wavelength enhancing range. The impedance gradient formed by the two or more acoustic matching layers 701 decreases transmission loss of sound waves, increases particle manipulation efficiency, facilitate improved in-line sound wave manipulation as compared to systems not including a matching layer, or a combination thereof.

According to one or more of the embodiments disclosed herein, the formation of multiple portions having alignment features 504, the transducer 111 detachably secured to the flow chamber 101, and/or the electrical coupling of the transducer 111 to the system interface 510 increases manufacturing efficiency, decreases manufacturing cost, provides disposable components and/or flow chambers 101, or a combination thereof. For example, in one embodiment, after providing a biological or hazardous fluid to the flow chamber 101, the transducer 111 is detached and the flow chamber 101 or a portion 501, 502 of the flow chamber 101 is discarded. The detached transducer 111 is then re-used with another flow chamber 101, facilitating repeated use of a single transducer with one or more different flow chambers. Additionally or alternatively, the flow chamber 101 and/or a portion 501, 502 of the flow chamber 101 is sterilized, such as, for example, with wet/steam sterilization, dry heat sterilization, ethylene oxide, sporicidal chemicals, glass plasma, irradiation, or a combination thereof. The transducer 111 is then attached or re-attached to the sterilized flow chamber 101, facilitating re-use of the transducer 111 and/or flow chamber 101.

Figure 9:
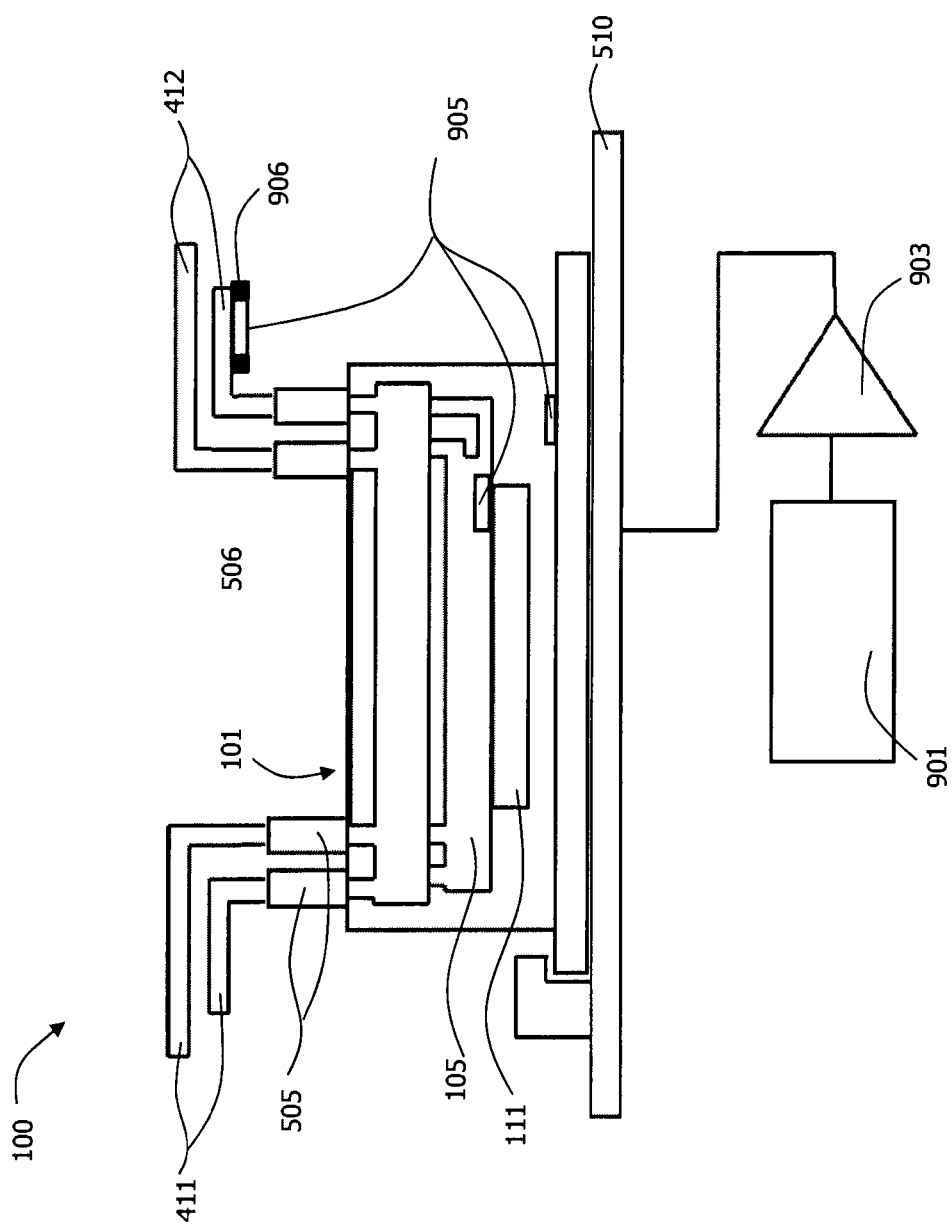
FIG. 9 shows a section view of a system including sensors and a controller, according to an embodiment of the disclosure.

Referring to FIG. 9, in one embodiment, the system 100 includes a controller 901 and an electrical driver 903, such as, but not limited to, an amplifier or transistor. The controller 901 is operably coupled to the electrical driver 903, which is operably coupled to the transducer 111. In another embodiment, an information storage device is integral with and/or coupled to the flow chamber 101. The information storage device stores sound wave properties specific to the individual flow chamber 101 and/or the transducer positioned to at least partially facilitate the in-line sound wave manipulation. The sound wave properties include, but are not limited to, dimensions of the flow chamber 101, resonant frequency of the flow chamber 101, other flow chamber properties, resonant frequency of the transducer 111, bandwidth of the transducer 111, electrical impedance of the transducer 111, capacitance of the transducer 111, temperature of the transducer 111, power of the transducer 111, operational life information of the transducer 111, other transducer properties, temperature of the fluid within the flow chamber 101, flow rates of the fluid within the chamber 101, other fluid properties, or a combination thereof.

In a further embodiment, the information storage device provides the sound wave properties to the controller 901, and the controller 901 sets and/or adjusts one or more parameters of the system 100 based upon the sound wave properties provided by the information storage device. For example, upon connecting the transducer 111, the system interface 510, and/or the controller 901 to the flow chamber 101, the information storage device provides the sound wave properties of the flow chamber 101 to the controller 901, which sets and/or adjusts the drive parameters of the electrical driver 903 and/or the transducer 111 according to the specific sound wave properties of the flow chamber 101. By providing the sound wave properties specific to each individual flow chamber 101, the information storage device facilitates re-use of the transducer 111, use of a single transducer 111 with a plurality of different flow chambers 101, use of a plurality of transducers 111 with a single flow chamber 101, increased operational efficiency, or a combination thereof.

Additionally or alternatively, the controller 901 is configured to receive at least one property measured by one or more sensors 905 in the system 100. In response to the at least one property measured by the one or more sensors 905, the controller 901 maintains or adjusts the parameters of the system 100. For example, in one embodiment, the controller 901 adjusts the electrical driving waveform of the transducer 111 in response to changes in the properties of the fluid and/or the transducer 111 that impact the in-line sound wave manipulation. The adjustment of the electrical driving waveform modifies the frequency, phase, and/or shape of a sound wave generated by the transducer 111, which facilitates selective responses to changes in fluid conditions.

The one or more sensors 905 include any suitable sensor for measuring a property of the transducer 111 and/or the fluid within the fluid receiving portion 105, such as, but not limited to, pressure, capacitance, flow rate, viscosity, sound wave profile, composition, presence of a bubble, or a combination thereof. Each of the sensors 905 is positioned within the system 100, integrally or detachably secured to a surface within the system 100, embedded within the system 100, and/or in direct or nearly direct contact with the fluid in the fluid receiving portion 105. For example, in one embodiment, one or more sensor retaining portions 906 are formed in the system 100, each of the sensor retaining portions 906 being configured to receive, retain, and/or align one or more of the sensors 905 therein.

One suitable sensor 905 includes a pressure sensor, such as, but not limited to, a PVDF piezo-polymer sensor, an MEMS pressure sensor, or a combination thereof. In one embodiment, the pressure sensor is secured to an inner surface of the fluid receiving portion 105 and/or an outer surface of the chamber body 103, opposite the transducer 111. In another embodiment, the pressure sensor is configured to detect a pressure field generated by the transducer 111. In a further embodiment, the pressure sensor records a minimum in the detected pressure field as compared to a transducer drive frequency, which is a combined resonance of the transducer 111 and the flow chamber 101.

Another suitable sensor 905 includes a strain sensor. In one embodiment, the strain sensor includes the divider 201 formed from PVDF or any other piezo-polymer. In another embodiment, the piezo-polymer divider includes an electrode pattern configured to measure strain, the measured strain being indicative of a differential laminar flow between the two or more fluids within the fluid receiving portion 105.

Additionally or alternatively, the sensor 905 includes a color sensor, such as, but not limited to, a dedicated color sensor, a red light-emitting diode (LED) and a photo-sensor, or a combination thereof. The color sensor is in direct or nearly direct contact with the fluid flow through the fluid receiving portion 105, and in one embodiment, is embedded in the chamber body 103. In another embodiment, the color sensor measures the color of the fluid in the fluid receiving portion 105, facilitating determination of certain fluid types based upon the measured color. For example, measuring a red color in the fluid receiving portion 105 indicates the presence of blood in certain embodiments. In a further embodiment, the color sensor includes a dedicated infrared (IR) LED and an IR diode sensor, a dedicated pulse-echo transducer, such as those made from PZT and/or PVDF, or a combination thereof. The dedicated IR LED and IR diode sensor are configured to measure an infrared response of the fluid within the fluid receiving portion 105, while the dedicated pulse-echo transducer is configured to measure sound wave backscatter of the fluid within the fluid receiving portion 105.

In one embodiment, one or more of the sensors 905 includes a capacitance sensor. In another embodiment, the capacitance sensor includes two opposing metalized surfaces of the chamber body 103, the two opposing metalized surfaces forming two electrodes of a capacitor or capacitor-like structure. The capacitance sensor measures a capacitance of the two opposing metalized surfaces, facilitating a determination of the contents of the fluid receiving portion 105. For example, based upon the measure capacitance, the capacitance sensor facilitates a determination as to whether the fluid is present in the fluid receiving portion 105. In a further embodiment, at least one of the surfaces of the chamber body 103 is formed from a piezo active material, such as PVDF, and metalized to form a series of sub-elements. Pulsing each of the sub-elements and recording an ultrasonic echo therefrom indicates whether a bubble is present in the fluid receiving portion 105.

Figure 10:
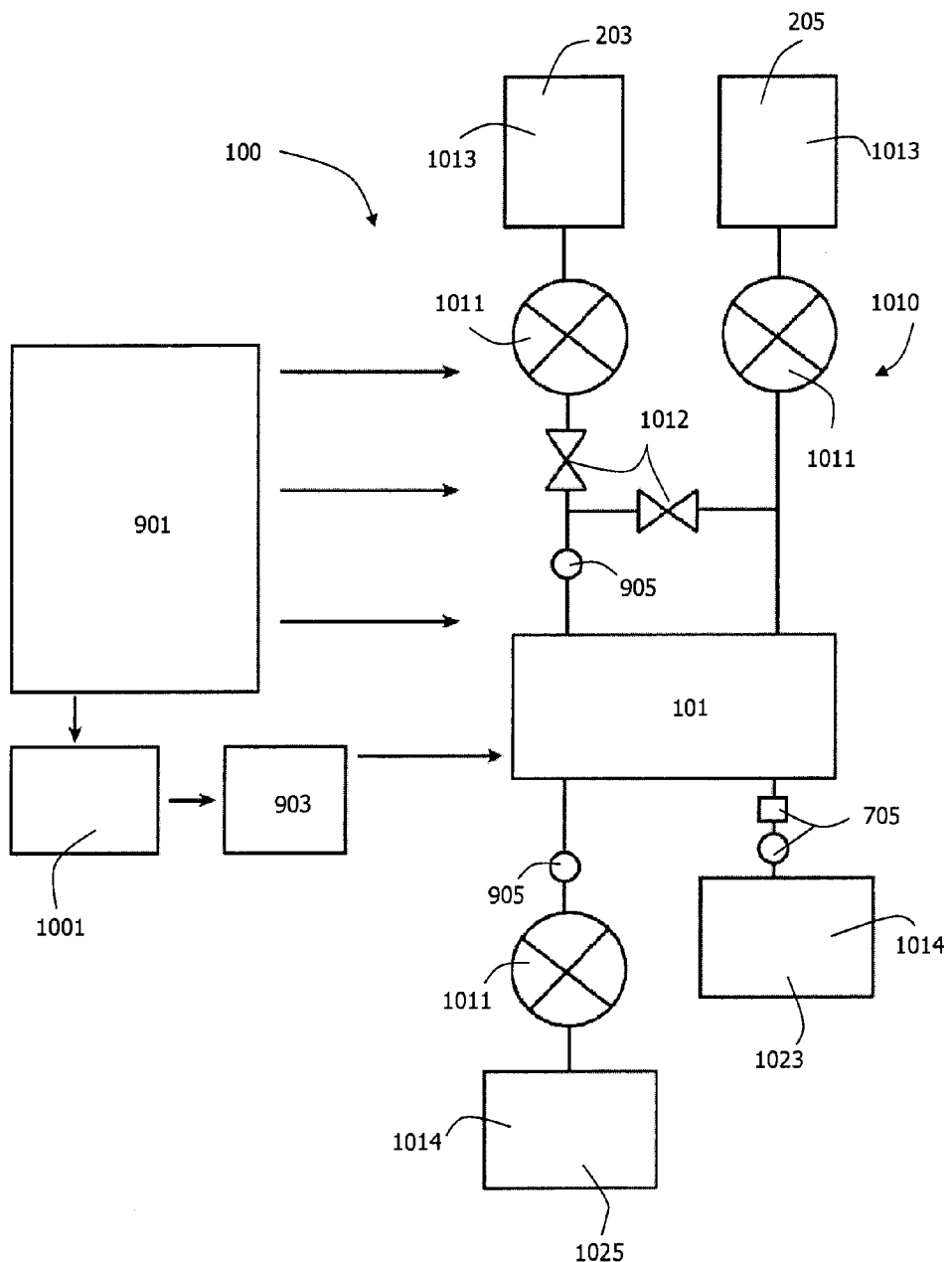
FIG. 10 shows a schematic view of a system, according to an embodiment of the disclosure.
Figure 11:
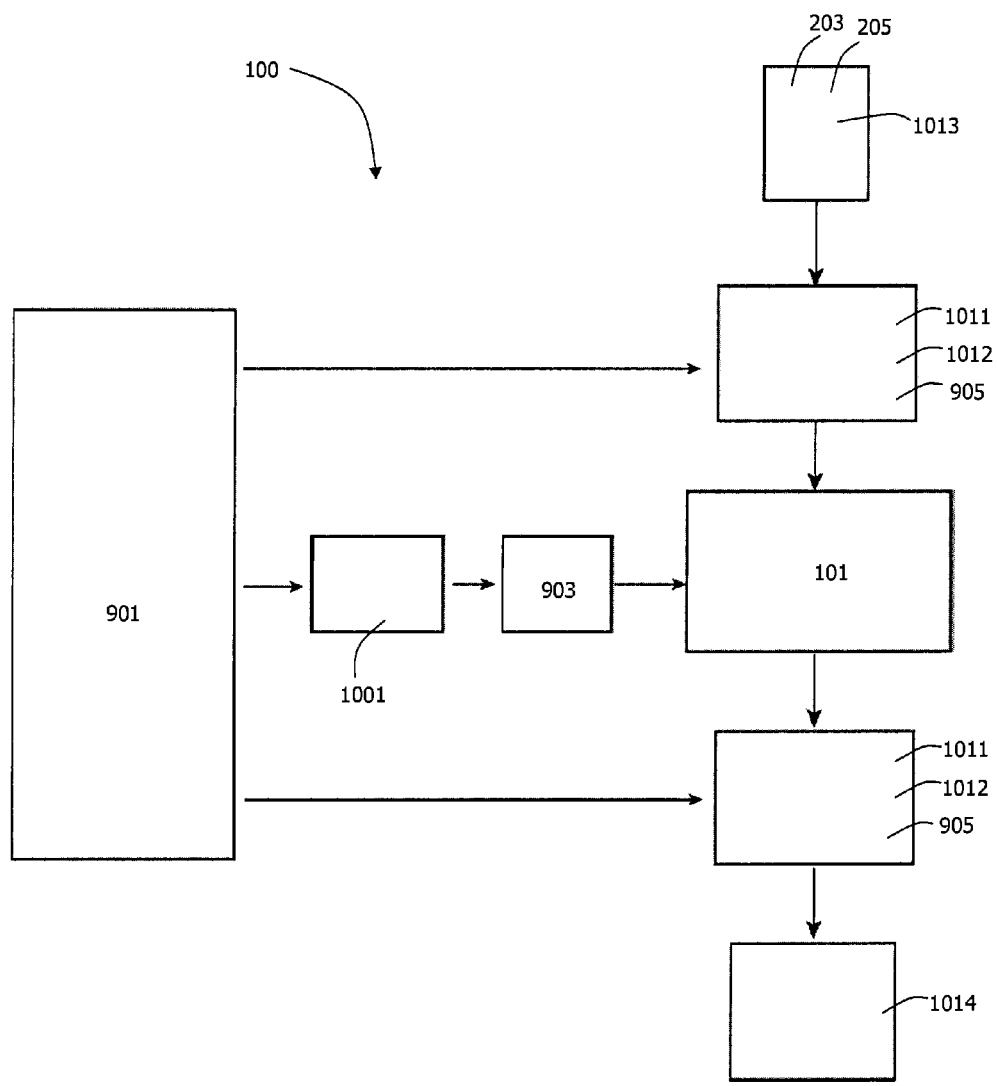
FIG. 11 shows an alternate schematic view of a system, according to an embodiment of the disclosure.
Figure 12:
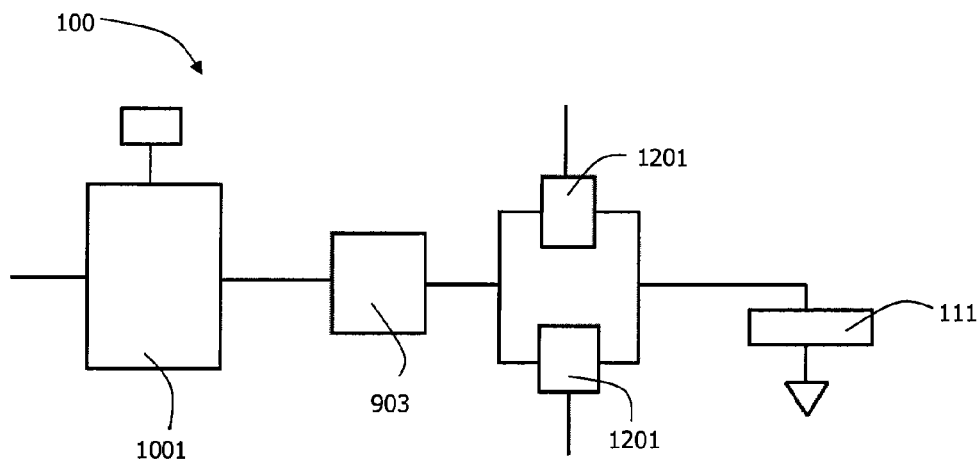
FIG. 12 shows a schematic view of a system including one or more switching elements, according to an embodiment of the disclosure.
Figure 13:
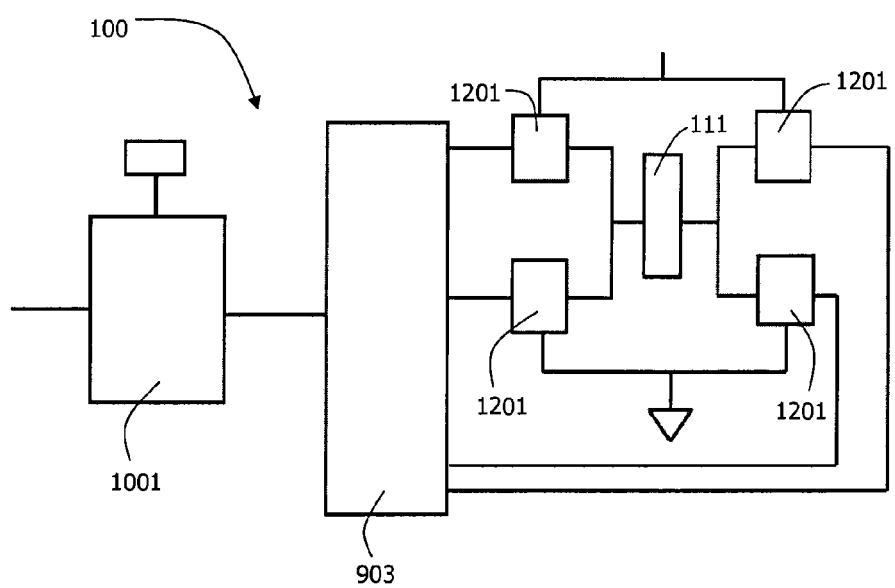
FIG. 13 shows an alternate schematic view of a system including one or more switching elements, according to an embodiment of the disclosure.

Referring to FIGS. 10-13, in one embodiment, the system 100 includes a frequency generator 1001 operably coupled to the electrical driver 903. The frequency generator 1001 includes any suitable generator such as, but not limited to, a sine-wave signal generator, a pulse-width-modulation drive, a square wave drive, or a combination thereof. The pulse-width-modulation drive and/or the square wave drive provide a decreased complexity, decreased cost, and/or increased manipulation efficiency as compared to the sine-wave signal generator. In another embodiment, as illustrated in FIGS. 12-13, the system 100 includes one or more switching elements 1201, such as, but not limited to, a field-effect transistor (FET), a metal-oxide-semiconductor field-effect transistor (MOSFET), an n-channel MOSFET, a p-channel MOSFET, or a combination thereof. The one or more switching elements 1201 are positioned to provide a desired voltage and/or current waveform across the transducer 111. For example, in a further embodiment, the switching elements 1201 provide the voltage and/or current waveform from a time average of a high speed switching signal. Additionally or alternatively, the one or more switching elements 1201 provide a square wave voltage and/or current waveform across the transducer 111 with a main frequency for driving the transducer 111. Turning to FIG. 13, in one embodiment, the one or more switching elements 1201 are positioned in a full wave bridge format, providing the voltage and/or current waveform across the transducer 111 using a single voltage source.

In certain embodiments, the system 100 is configured to monitor a frequency of the transducer 111 and/or maintain the frequency of the transducer 111 within a predetermined bandwidth, such as, but not limited to, the resonance frequencies of the system 100. For example, in one embodiment, as illustrated in FIGS. 10-11, the system 100 includes a feedback arrangement, in which the controller 901 maintains or adjusts the frequency of the transducer 111 in response to frequency information received from the one or more sensors 905. In another embodiment, the system 100 includes an electrical matching circuit configured to suppress frequencies outside of the predetermined bandwidth. The electrical matching circuit is positioned in series or parallel orientation between the electrical driver 903 and the transducer 111, and includes any circuit for increasing and/or decreasing the electrical energy supplied to the transducer 111. Suitable electrical matching circuits include, but are not limited to, resistors, capacitors, inductors, transformers, frequency filters, or a combination thereof. The maintaining of the transducer 111 within the predetermined bandwidth increases an efficiency of the transducer 111 and/or the system 100 as compared to transducers and/or systems operating outside the resonance frequency and/or predetermined bandwidth.

Figure 20:
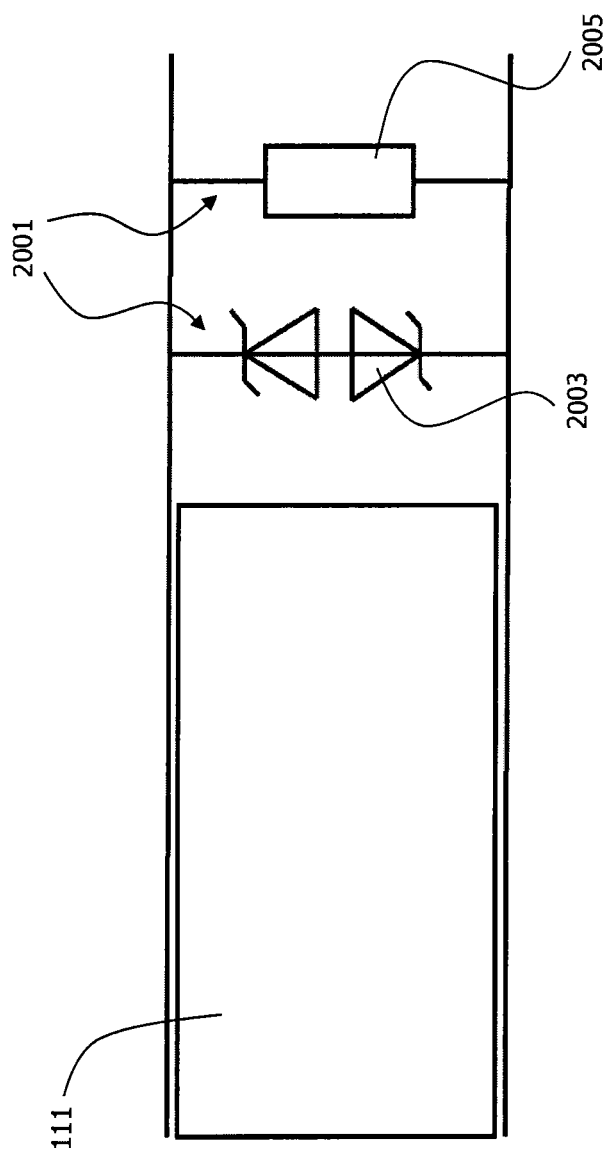
FIG. 20 shows a schematic view of a transducer coupled to a protection device, according to an embodiment of the disclosure.

Additionally or alternatively, as illustrated in FIG. 20, the transducer 111 is coupled to a protection device 2001. The protection device 2001 is configured to reduce or eliminate electrical charge build-up in the transducer 111, reducing or eliminating accidental discharges that damage the transducer 111. Suitable protection devices include, but are not limited to, a transient-voltage suppression (TVS) device 2003, a bleed resistor 2005, a zener diode, or a combination thereof.

Referring again to FIGS. 10-11, in one embodiment, the system 100 includes a fluid delivery arrangement 1010. In another embodiment, the fluid delivery arrangement 1010 includes at least one pump 1011 and/or at least one valve 1012. The at least one pump 1011 and/or the at least one valve 1012 are operably connected to the flow chamber 101, the controller 901, the one or more sensor 905, or a combination thereof. For example, in a further embodiment, the at least one pump 1011 and the at least one valve 1012 are connected to each other and/or the flow chamber 101 through any suitable tubing. The tubing is disposable, detachable from the flow chamber 101, and/or coupled to a fluid delivery interface to facilitate connecting and disconnecting the fluid delivery arrangement 1010 from one or more of the flow chambers 101. Additionally or alternatively, the at least one pump 1011 and the at least one valve 1012 are electrically coupled to the controller 901. The controller 901 operates the at least one pump 1011 and the at least one valve 1012 to set or adjust flow rate, flow sequence, flow time span, fluid composition, or a combination thereof. By operating the at least one pump 1011 and the at least one valve 1012, the controller 901 provides automatic sample delivery and processing, which decreases manual labor, decreases operating error, and/or increases efficiency.

Suitable pumps for use in the fluid delivery arrangement 1010 include, but are not limited to, syringe pumps, gear pumps, screw pumps, peristaltic pumps, rope pumps, or a combination thereof. In one embodiment, the at least one pump 1011 forces a pre-manipulation fluid through the system 100 prior to sound wave manipulation, the pre-manipulation fluid removing air from the tubing and/or the flow chamber 101. Suitable pre-manipulation fluids include, but are not limited to, phosphate-buffered saline (PBS), sodium chloride solution, additive solution formula 3 (AS-3), dextrose and sodium chloride processing solution, ethanol solution, isopropyl alcohol, acetone, and/or any other buffer solution. In another embodiment, the fluid delivery arrangement 1010 includes at least one sample reservoir 1013 and/or at least one collection reservoir 1014. For example, in a further embodiment, the fluid delivery arrangement 1010 forms a portion of a blood washing system, and includes two sample reservoirs 1013, three pumps 1011, two valves 1012, and two collection reservoirs 1014. One of the pumps 1011 generates a flow of the first fluid 203, such as blood, from one of the sample reservoirs 1013 to a first inlet in the flow chamber 101, while another pump 1011 generates a flow of the second fluid 205, such as buffer solution, from the other sample reservoir 1013 to a second inlet in the flow chamber 101. In a further embodiment, the first inlet and the second inlet are parallel or substantially parallel, facilitating laminar flow of the first fluid 203 and the second fluid 205 in the fluid receiving portion 105. The sound wave manipulation in the flow chamber 101 transfers at least one particle from the first fluid 203 to the second fluid 205, forming washed blood 1023 and waste 1025. The washed blood 1023 exits a first outlet in the flow chamber 101 and is collected in one of the collection reservoirs 1014, while the waste 1025 is drawn out of a second outlet in the flow chamber 101 with the third pump 1011 and collected in the other collection reservoir 1014.

Figure 14:
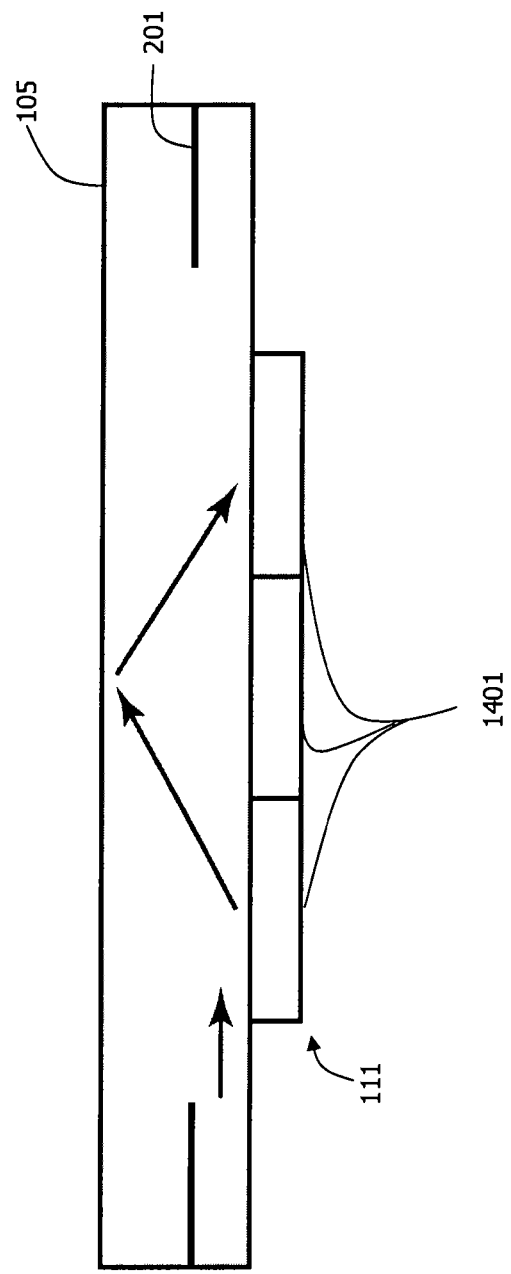
FIG. 14 shows a process view of a transducer arrangement configured to measure flow, according to an embodiment of the disclosure.

In one embodiment, the controller 901 is configured to adjust and/or maintain the flow rate of the at least one pump 1011 and/or the sound waves generated by the transducer 111 in response to measured flow rates of fluids within the flow chamber 101. The adjusting and/or maintaining of the flow rates and/or sound waves facilitates increased sound wave manipulation and/or increased manipulation efficiency of the system 100. In another embodiment, the transducer 111 is configured to measure the flow rates within the flow chamber 101. For example, as illustrated in FIG. 14, in a further embodiment, the transducer 111 is separated into two or more sections 1401, the two or more sections 1401 forming an arrangement of transducers configured to transmit and receive sound. Based upon the received sound, the transducer 111, the controller 901, and/or the system 100 determines the measured flow rates within the flow chamber 101.

Figure 15:
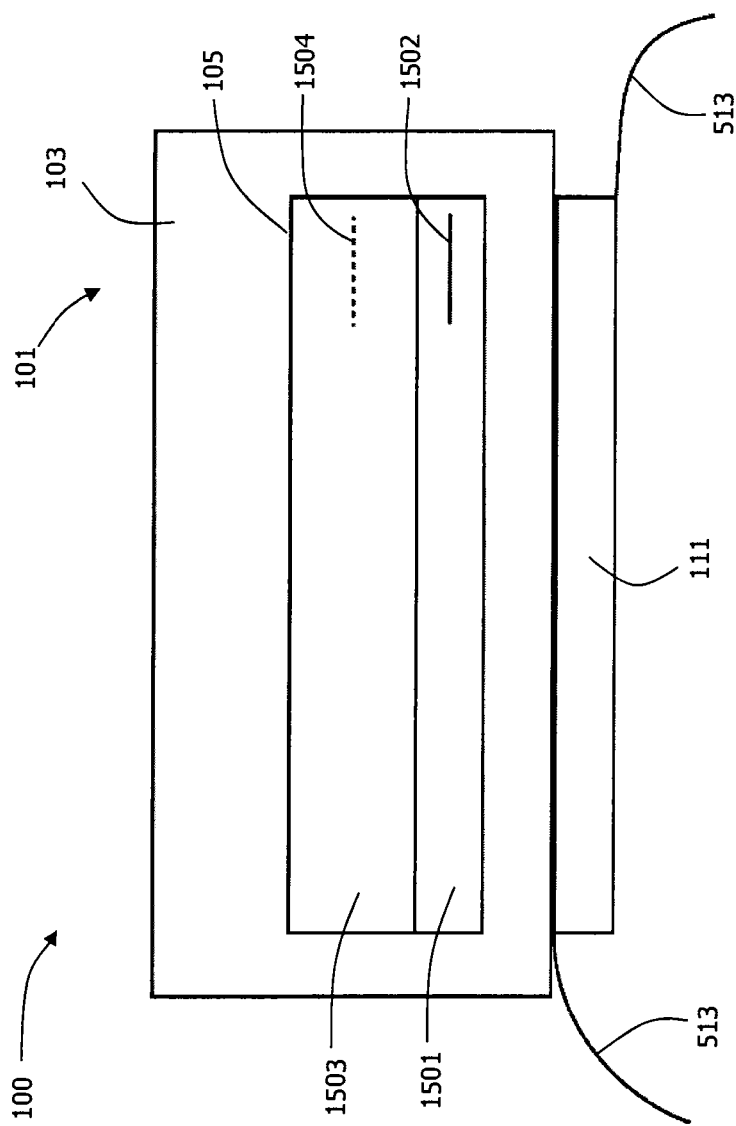
FIG. 15 shows a section view of two fluids positioned within a flow chamber, according to an embodiment of the disclosure.

Referring to FIG. 15, in one embodiment, the system 100 and/or the fluid delivery arrangement 1010 is configured to position relatively higher acoustic impedance fluids 1503 at an acoustic pressure node 1504 as they enter the fluid receiving portion 105, and relatively lower acoustic impedance fluids 1501 at an acoustic pressure antinode 1502 as they enter the fluid receiving portion 105. As used herein, the term relatively higher acoustic impedance refers to a fluid having an acoustic impedance that is higher than or equal to the acoustic impedance of the relatively lower acoustic impedance fluid. For example, certain concentrations of sodium chloride and/or dextrose/glucose solution have a higher acoustic impedance than water and/or blood. The initial positioning of the relatively higher acoustic impedance fluid 1503 at the acoustic pressure node 1504 reduces or eliminates vertical movement (in a direction from the pressure antinode to the pressure node) of the fluid 1501 within the flow chamber 101 upon the application of sound waves. Additionally, the reduction or elimination of vertical movement of the fluid 1501 within the flow chamber 101 reduces or eliminates fluid relocation and/or contamination within the flow chamber 101.

Figure 16:
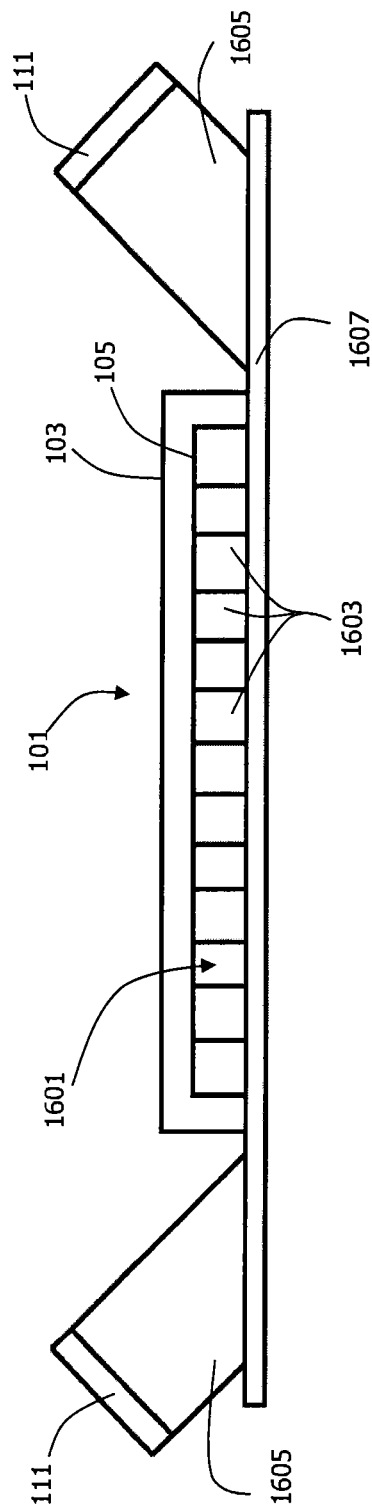
FIG. 16 shows a section view of a parallel flow system, according to an embodiment of the disclosure.

Turning to FIG. 16, in one embodiment, the flow chamber 101 is configured to generate two or more parallel flows 1601 of individual fluids 1603 through the fluid receiving portion 105. The two or more parallel flows 1601 are generated by any suitable configuration, such as, but not limited to, multiple inlets and/or outlets in the flow chamber 101. The individual fluids 1603 within the two or more parallel flows 1601 are the same as or different from at least one other fluid 1603 within the flow chamber 101. For example, in another embodiment, one of the fluids 1603 includes a sample fluid while another fluid includes sheath flow. In a further embodiment, the system 100 includes a three-dimensional (3D) chip configuration that generates the two or more parallel flows 1601 and/or provides the in-line sound wave manipulation of the individual fluids 1603. For example, one suitable 3D chip configuration includes the transducer 111 secured to an acoustic wedge 1605 positioned on a substrate 1607. The transducer 111 and the acoustic wedge 1605 facilitate sound wave manipulation of the two or more parallel flows 1601, such as, for example, movement of particle from the sample flow to the sheath flow for particle separation and/or medium exchange. The two or more parallel flows 1601 facilitate simultaneous processing of an increased amount of samples within a single flow chamber 101, which increases processing efficiency and/or increases sound wave manipulation throughput.

The system 100 according to one or more of the embodiments disclosed herein provides sound wave manipulation for applications including, but not limited to, blood component separation (for example, white blood cells (WBC), red blood cells (RBC), platelets, plasma), therapeutic (for example, transfusion), diagnostic, microorganism separation, microorganism enrichment, cancer cell separation, fetal cell separation, circulating endothelia cell separation, particle selection (for example, separation based on size; particle sizes from nm to mm scale), immune cell sorting (for example, for basic research), t-cell subpopulation sorting (for example, for immunotherapy), stem cell sorting (for example, for research and therapy), sperm sorting, bacteria sorting (for example, for basic research), chromosome sorting (for example, for genetic studies), vesicle isolation, exosome isolation, selection of fluorescent protein labeled cells, selection of cells for antibody production, cell wash, particle medium exchange, or a combination thereof. As will be appreciated by those skilled in the art, the terms "particles" and "particulate" are intended to encompass all of the above-referenced organic, inorganic, living, or non-living constituents.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A manipulation system, comprising:
    a flow chamber arranged and disposed to receive a fluid containing a particulate and provide sound wave manipulation of at least a portion of the particulate from the fluid; and
    a transducer positioned externally of a portion of the flow chamber receiving fluid flow to facilitate the sound wave manipulation within the flow chamber;
    an electrical matching circuit operably connected with the transducer for adjusting the sound wave manipulation in response to one or more sensors configured for measuring an impedance of the transducer,
    wherein the adjusting the sound wave manipulation includes matching an impedance of an electrical signal provided to the transducer with the measured impedance of the transducer.

2. The manipulation system of claim 1, further comprising electrical interface elements in thermal communication with the transducer for transferring heat from the transducer during the sound wave manipulation.

3. The manipulation system of claim 1, wherein the transducer is detachable from the flow chamber.

4. The manipulation system of claim 3, wherein the flow chamber is configured to be sterilized.

5. The manipulation system of claim 1, wherein the flow chamber is manufactured with a process selected from the group consisting of injection molding, chemical etching, computer numerical control (CNC) machining, laser cutting, vacuum molding, and combinations thereof.

6. The manipulation system of claim 1, further comprising an acoustic matching layer positioned between the flow chamber and the transducer, wherein a thickness of the acoustic matching layer is controlled by the formula N/2*L+L/4, where L is a wavelength and N is an integer corresponding to the number of half wavelengths fitting between the nodes.

7. The manipulation system of claim 1, further comprising a fluid delivery system operably connected to the flow chamber, the fluid delivery system being arranged and disposed to automatically control a fluid delivery from the fluid delivery system to the flow chamber, a flow sequence, a flow rate, a flow time span, a fluid composition, or combinations thereof.

8. The manipulation system of claim 1, wherein the transducer is cut into a matrix of individual transducer elements selected from the group consisting of rods, strips, and combinations thereof.

9. The manipulation system of claim 1, wherein the electrical matching circuit is arranged and disposed to adjust an electrical driving power provided to the transducer, a driving frequency of the sound waves provided by the transducer, a phase of the sound waves provided by the transducer, a shape of the sound waves provided by the transducer, or combinations thereof.

10. The manipulation system of claim 1, wherein the electrical matching circuit is further configured for modifying a frequency, a phase, a shape and an energy of the sound waves manipulated by the transducer.

11. The manipulation system of claim 1, wherein the transducer is driven by at least one of a pulse-width-modulation and/or a square wave drive.

12. The manipulation system of claim 1, further comprising:
a protection device operably connected to the transducer;
wherein the protection device being arranged and disposed to decrease at least one of electrical charge build-up within the transducer and electrical charge discharge to the transducer.

13. The manipulation system of claim 1, wherein the transducer further comprises a composite piezoelectric positioned to provide sound waves for the sound wave manipulation.

14. The manipulation system of claim 1, wherein the one or more sensors are further configured for measuring a resonant frequency of the transducer, a bandwidth of the transducer, an electrical impedance of the transducer, a capacitance of the transducer, a resonant frequency of the flow chamber, flow rates of the fluid within the flow chamber, a temperature of the transducer, a power of the transducer, an operational life information of the transducer, an operational life information of the flow chamber, or combinations thereof.

15. The manipulation system of claim 1, further comprising a divider within the flow chamber.

16. The manipulation system of claim 1, further comprising a hydrophilic coating on an interior of the flow chamber for removing bubbles.

17. The manipulation system of claim 1, further comprising a plurality of grooves or bumps positioned on an interior of the flow chamber for removing bubbles.

18. The manipulation system of claim 1, wherein the one or more sensors are arranged and disposed to further measure a property of the particulate, the transducer, or combinations thereof.

19. The manipulation system of claim 1, wherein the flow chamber includes at least a first portion and a second portion, the first portion being secured to the second portion and aligned using alignment features for creating the portion of the flow chamber receiving fluid flow, wherein the alignment features are clamping features, corresponding projections and recesses, overlapping portions, posts and corresponding apertures, or a combination thereof.

20. The manipulation system of claim 1, further comprising an electrical matching circuit operably connected with the transducer for adjusting the sound wave manipulation in response to one or more sensors configured for measuring an impedance of the transducer, wherein the adjusting the sound wave manipulation includes matching an impedance of an electrical signal provided to the transducer with the measured impedance of the transducer.

21. The manipulation system of claim 20, wherein the electrical matching circuit is further configured for adjusting a power provided to the transducer, a frequency of the sound waves, a phase of the sound waves, a shape of the sound waves, or combinations thereof.

22. The manipulation system of claim 20, wherein the one or more sensors are further configured for measuring a resonant frequency of the transducer, a bandwidth of the transducer, an electrical impedance of the transducer, a capacitance of the transducer, a temperature of the transducer, a power of the transducer, an operational life information of the transducer, or combinations thereof.

23. The manipulation system of claim 20, wherein a property of the fluid within the flow chamber includes strain, resistance, pressure, temperature capacitance, flow rate, viscosity, sound wave profile, composition, presence of a bubble or combinations thereof.

24. A method of using a manipulation system, comprising: passing liquid containing a particulate through a flow chamber;
a transducer, positioned externally of a portion of the flow chamber receiving fluid flow, manipulating at least a portion of the particulate within the flow chamber by producing sound waves propagating through the flow chamber; one or more sensors measuring an impedance of the transducer: and an electrical driver operably coupled to the transducer adjusting an impedance of an electrical signal provided to the transducer to match the measured impedance of the transducer.

25. A manipulation system, comprising:
a flow chamber arranged and disposed to receive a fluid containing a particulate and provide sound wave manipulation of at least a portion of the particulate from the fluid; and
a transducer positioned externally of a portion of the flow chamber receiving fluid flow to facilitate the sound wave manipulation within the flow chamber;
an acoustic matching layer positioned between the flow chamber and the transducer, wherein a thickness of the acoustic matching layer is controlled by the formula N/2*L+L/4, where L is a wavelength and N is an integer corresponding to the number of half wavelengths fitting between the nodes.

26. The manipulation system of claim 25, further comprising electrical interface elements in thermal communication with the transducer for transferring heat from the transducer during the sound wave manipulation.

27. The manipulation system of claim 25, wherein the transducer is detachable from the flow chamber.

28. The manipulation system of claim 25, wherein the flow chamber is configured to be sterilized.

29. The manipulation system of claim 25, wherein the flow chamber is manufactured with a process selected from the group consisting of injection molding, chemical etching, computer numerical control (CNC) machining, laser cutting, vacuum molding, and combinations thereof.

30. The manipulation system of claim 25, further comprising a fluid delivery system operably connected to the flow chamber, the fluid delivery system being arranged and disposed to automatically control a fluid delivery from the fluid delivery system to the flow chamber, a flow sequence, a flow rate, a flow time span, a fluid composition, or combinations thereof.

31. The manipulation system of claim 25, wherein the transducer is cut into a matrix of individual transducer elements selected from the group consisting of rods, strips, and combinations thereof.

32. The manipulation system of claim 25, wherein the transducer is driven by at least one of a pulse-width-modulation and/or a square wave drive.

33. The manipulation system of claim 25, further comprising:
a protection device operably connected to the transducer;
wherein the protection device being arranged and disposed to decrease at least one of electrical charge build-up within the transducer and electrical charge discharge to the transducer.

34. The manipulation system of claim 25, wherein the transducer further comprises a composite piezoelectric positioned to provide sound waves for the sound wave manipulation.

35. The manipulation system of claim 25, wherein the flow chamber includes at least a first portion and a second portion, the first portion being secured to the second portion and aligned using alignment features for creating the portion of the flow chamber receiving fluid flow, wherein the alignment features are clamping features, corresponding projections and recesses, overlapping portions, posts and corresponding apertures, or a combination thereof.

36. The manipulation system of claim 25, further comprising a divider within the flow chamber.

37. The manipulation system of claim 25, further comprising a hydrophilic coating on an interior of the flow chamber for removing bubbles.

38. The manipulation system of claim 25, further comprising a plurality of grooves or bumps positioned on an interior of the flow chamber for removing bubbles.

* * * * *